United States Patent [19]

Kikuchi et al.

[11] Patent Number: 5,033,478
[45] Date of Patent: Jul. 23, 1991

[54] HEATING APPARATUS FOR HYPERTHERMIA

[75] Inventors: Makoto Kikuchi, Mitaka; Shinsaku Mori, Tokyo; Yoshio Nikawa, Tokyo; Takashige Terakawa, Tokyo, all of Japan

[73] Assignee: Tokyo Keiki Co., Ltd., Tokyo, Japan

[21] Appl. No.: 335,841

[22] Filed: Apr. 10, 1989

Related U.S. Application Data

[62] Division of Ser. No. 121,145, Nov. 16, 1987, Pat. No. 4,860,770, which is a division of Ser. No. 756,071, Jul. 17, 1985, Pat. No. 4,747,416.

[30] Foreign Application Priority Data

| Jul. 24, 1987 | [JP] | Japan | 59-153678 |
| Jul. 24, 1987 | [JP] | Japan | 59-153679 |
| Jul. 24, 1987 | [JP] | Japan | 59-153680 |
| Jul. 24, 1987 | [JP] | Japan | 59-153681 |
| Jul. 24, 1987 | [JP] | Japan | 59-153682 |

[51] Int. Cl.$^5$ .............................. A61N 5/02
[52] U.S. Cl. .................... 128/804; 128/400; 128/402; 219/10.55 R
[58] Field of Search ............... 128/804, 421–423 R, 128/399, 402; 219/10.55 R, 10.55 A, 10.55 B, 10.55 F

[56] References Cited

U.S. PATENT DOCUMENTS

| 3,077,195 | 5/1963 | Folsche . |
| 4,108,147 | 8/1978 | Kantor . |
| 4,140,130 | 2/1979 | Storm, III . |
| 4,204,549 | 5/1980 | Paglione . |
| 4,228,809 | 10/1980 | Paglione . |
| 4,282,887 | 8/1981 | Sterzer . |
| 4,341,227 | 7/1982 | Turner . |
| 4,397,313 | 8/1983 | Vaguine . |
| 4,397,314 | 8/1983 | Vaguine . |
| 4,403,618 | 9/1983 | Turner et al. . |
| 4,446,874 | 5/1984 | Vaguine . |
| 4,462,412 | 7/1984 | Turner . |
| 4,530,358 | 7/1985 | Forssmann . |
| 4,586,516 | 5/1986 | Turner . |
| 4,589,424 | 5/1986 | Vaguine . |
| 4,601,296 | 7/1986 | Yerushalmi . |

FOREIGN PATENT DOCUMENTS

| 0111386 | 6/1984 | European Pat. Off. . |
| 1440333 | 4/1969 | Fed. Rep. of Germany . |
| 2060923 | 7/1971 | Fed. Rep. of Germany . |
| 2648908 | 5/1978 | Fed. Rep. of Germany . |
| 0028338 | 3/1977 | Japan . |

OTHER PUBLICATIONS

"Hyperthermia in Cancer Therapy", by F. Kristian Storm, M.D., G. K. Hall, Med. Pub. 1983, Title page and table of contents.
Magin, "A Microwave System . . . Animals", IEEE Trans. Microwave Theory & Tech., MTT-27, No. 1, pp. 78-83, Jan. 1979.
Robinson et al., "Techniques . . . Hyperthermia . . . Cannoma", IEEE Trans. Microwave Theory & Tech., MTT-26, No. 8, pp. 546-549, Aug. 1978.
"A Localized Current Field . . . ", by Astrahan et al, Med. Phys 9(3), May/June 1982, pp. 419-424.
The October 1976 issue of Microwaves, article entitled: "Microwaves Score TKO in Fight Against Cancer".

*Primary Examiner*—Lee S. Cohen
*Attorney, Agent, or Firm*—Sandler, Greenblum & Bernstein

[57] ABSTRACT

A heating apparatus for hyperthermia utilizes electromagnetic waves for locally heating cancerous cells within a living body. When it is necessary for a plurality of patients to be subjected to hyperthermia treatment at the same time and in parallel with each other, the control of a plurality of electromagentic wave outputs and the control of cooling of the surface of a heated region are effected by a centralized control which employs time-division multiplexing. Thus, it is advantageously possible to efficiently carry out a hyperthermia treatment which is fitting for the condition of each of a plurality of patients.

10 Claims, 26 Drawing Sheets

FIG. 12

```
MAGNETRON OUTPUT OFF
        │
       100
        ▼
    ┌────────┐
    │  111   │── MEASURE SURFACE
    └────────┘   TEMPERATURE AND
        │        INTERNAL TEMPERATURE
        ▼
    ◇ 120 HEATING END ?
   Y/    \N
  END     │
  130     ▼
(90 in   ◇ 121 SURFACE TEMPERATURE
 Fig.11)   HIGHER THAN SET VALUE ?
         N│                  Y│
          ▼                   ▼
    ┌──────────────┐    ┌──────────────┐
    │ CLOSE VALVE  │    │ START HEATING│ 180
    │ BY ONE STEP  │122 │ TIME MEASURE-│
    └──────────────┘    │    MENT      │
          │             └──────────────┘
          ▼                   │
    ◇ 140 INTERNAL            ▼
      TEMPERATURE       ┌──────────────┐
      HIGHER THAN       │ POWER ONE    │ 190
      SET VALUE ?       │ STEP DOWN    │
       Y/  \N           └──────────────┘
         ◇ 150                │
         POWER                ▼
         MAXIMUM?       ┌──────────────┐
        Y│  \N          │ OPEN VALVE BY│ 191
         │   ▼          │ ONE STEP     │
         │  ┌─────────┐ └──────────────┘
         │  │POWER ONE│        │
         │  │STEP UP  │160     │
         │  └─────────┘        │
         ▼    │                ▼
    ┌──────────┐          ┌──────────┐
    │MAGNETRON │          │MAGNETRON │
    │OUTPUT ON │170       │OUTPUT OFF│ 200
    └──────────┘          └──────────┘
         │                     │
         └──────────┬──────────┘
                    ▼
               (90 in Fig.11)
```

HEATING APPARATUS FOR HYPERTHERMIA

This is a division of application Ser. No. 121,145 filed Nov. 16, 1987, now U.S. Pat. No. 4,860,770, which is a Divisional of application Ser. No. 756,071 filed on July 17, 1985, now U.S. Pat. No. 4,747,416.

BACKGROUND OF THE INVENTION

1. Field of the Invention

The present invention relates to a heating apparatus for hyperthermia and, more particularly, to a heating apparatus for hyperthermia which deteriorates the regenerative functions of cancerous cells by heating them with electromagnetic waves, thereby liquidating these cancerous cells.

2. Description of the Prior Art

In recent years, hyperthermia has been given wide attention and papers have been written on hyperthermia, a therapy which deteriorates the regenerative functions of cancerous cells and thereby liquidates significant portions of them by applying heat of approximately 43° C. for one or two hours and repeating the treatment at certain intervals. (MICROWAVES. October, 1976).

There are two kinds of hyperthermia therapy: general and local heating methods. Three methods have been proposed for local heating: one utilizes electromagnetic waves, the second uses electric conduction and the third uses ultrasonic waves.

Researchers have concluded that the optimum temperature for attacking cancerous cells is 43° C. or thereabouts. Temperatures below this will weaken the effects and temperatures above this will damage normal cells. Hyperthermia aims at liquidating without heating normal cells by maintaining the temperature in a confined narrow range.

However, it has been quite difficult when utilizing conventional means to keep the temperature of cancerous cells at approximately 43° C. for one or two hours due to the peculiar functions of a living body. In particular, heating by electromagnetic waves has been put aside for a long time because a significant portion of the electromagnetic waves is absorbed by the body surface and this method is thus unfit for heating regions deep within the body. In view of the above-described circumstances, the inventors of the present invention have previously proposed a heating apparatus for hyperthermia utilizing electromagnetic waves which is provided with a function which enables accurate control of the temperature of a given heated region in a living body such that this temperature is maintained at a predetermined value over a certain period of time.

Hyperthermia takes a relatively long period of time (about one hour) for a single treatment and requires that this treatment be repeated periodically, which fact involves an unfavorably long overall treatment time. In consequence, treating a large number of patients at the same time requires a correspondingly large number of devices and unfavorably increases the cost of installing equipment for treatment.

SUMMARY OF THE INVENTION

It is an object of the present invention to provide a heating apparatus for hyperthermia which is provided with a function which enables the simultaneous and parallel heating of given regions within the bodies of a plurality of patients utilizing electromagnetic waves through control effected from the center of a hyperthermia system, thereby allowing an increase in the efficiency of the hyperthermia treatment and a reduction in the cost of installing equipment for treatment.

It is another object of the invention to provide a heating apparatus for hyperthermia which is provided with a function which enables heating temperatures to be set which are different for each patient even in the case of simultaneous hyperthermia treatment conducted for a plurality of patients by control effected from the center of a hyperthermia system and which also enables the temperatures set to be optimally controlled over a long period of time and with high accuracy.

It is still another object of the invention to provide a heating apparatus for hyperthermia which is provided with a function which enables the prevention of any thermal burn and the alleviation of any pains which patients may suffer by effecting an optimal cooling control in which the rise in temperature at the surface of the heated region of a patient, which differs for each patient, is optimally controlled even in the case of simultaneous hyperthermia treatment conducted for a plurality of patients by control effected from the center of a hyperthermia system.

BRIEF DESCRIPTION OF THE DRAWINGS

FIGS. 11 and 12 are flow charts which show the operation of the embodiment illustrated in FIG. 10;

DETAILED DESCRIPTION OF THE PREFERRED EMBODIMENTS

First Embodiment

A first embodiment of the present invention will be described hereinunder with reference to FIGS. 1 to 9.

Figure 1:
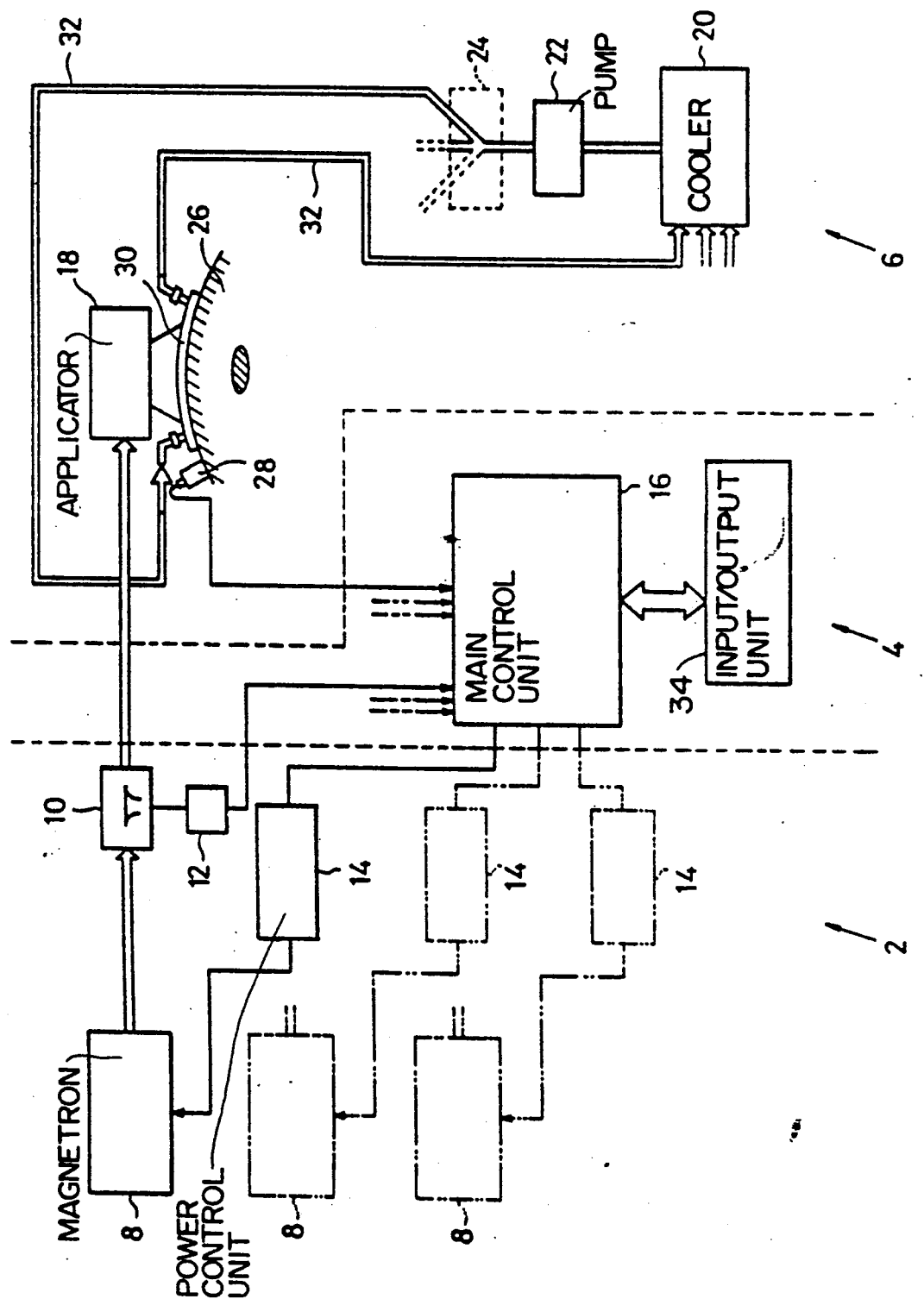
FIG. 1 is a general system diagram of a first embodiment of the present invention.

FIG. 1 is a general system diagram of the first embodiment. In this embodiment, a heating apparatus for hyperthermia consists essentially of a microwave generating section 2 which serves as an electromagnetic wave generating section, a control section 4 which includes control means, and a microwave irradiating section 6.

The microwave generating section 2 is composed of: magnetrons 8 which serve as electromagnetic wave generating means for simultaneously irradiating three patients (the number of patients assumed is the same throughout the embodiments described hereinafter) with electromagnetic waves; directional couplers 10 which are disposed on the respective output sides of the magnetrons 8; diodes 12 which serve as sensors for detecting the respective output levels of the magnetrons 8 through the respective directional couplers 10; and power control units 14 which adjust the respective outputs of the magnetrons 8. Each of the power control units 14 is adapted to adjust the output of the associated magnetron 8 by changing the anode voltage of the magnetron 8 which is controlled by a thyristor. Each of the directional couplers 10 has a function of isolating incident and reflected waves from each other and individually taking them out. The electromagnetic waves taken out by the directional couplers 10 are respectively detected by the diodes 12 and converted into voltages, each of which is then delivered to a main control unit 16 in the control section 4 through an analog-to-digital converter, not shown, (referred to simply as an "A/D converter", hereinafter).

The main control unit 16 obtains a difference between the respective power level values of the incident and reflected waves taken out, thereby calculating the power level of the microwave which is to be effectively supplied to each of the applicators 18 (described later) provided in the microwave irradiating section 6. The main control unit 16 controls the output of each of the magnetrons 8 on the basis of the result of this calculation.

The microwave irradiating section 6 in this embodiment is composed of: applicators 18 each irradiating a living body 26 with microwaves; a cooler 20 which cools a coolant for cooling the opening side of each applicator 18, that is, the surface of the body 26; a pump 22 which recirculates the coolant cooled by the cooler 20; and a branching circuit 24 for supplying the coolant to each applicator 18. The microwave irradiating section 6 further includes internal temperature sensors 28 which serve as internal temperature detecting means and each which detects the temperature of cancerous cells inside the corresponding body 26, each internal temperature sensor 28 being stuck into a part of the body 26 where the hyperthermia treatment is taking place. Illustration of the portions of microwave irradiating section 6 for the other two patients is omitted (the same is the case with each of the embodiments described hereinafter).

Figure 2:
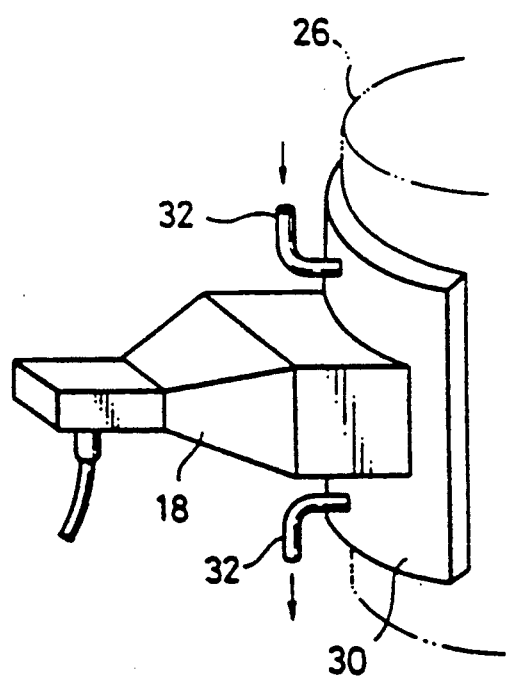
FIG. 2 is a perspective view of one example of an applicator.

Each applicator 18 is an antenna which is, as shown in FIG. 2, brought into close contact with the surface of the corresponding body 26 and irradiates the body 26 with electromagnatic waves for the purpose of heating targeted cancerous cells. Each applicator 18 has a cooling member 30 provided on the surface thereof which contacts the surface of the body 26 in order to prevent the skin thereof from being thermally burnt which would be caused by the heat generated as the result of dielectric losses in the skin at the area of contact of the body 26. Each of the cooling members 30 is provided with a pipe 32 for passing water which is employed as a coolant (the same is the case with each of the embodiments described hereinafter). In consequence, the water which is cooled in the cooler 20 is forcedly recirculated through each cooling member 30 by the operation of the pump 22, thereby cooling the opening side of each applicator 18, that is, the surface of the corresponding body 26.

Each internal temperature sensor 28 detects the temperature of cancerous cells, and the output of the corresponding magnetron 8 is adjusted by the main control unit 16 on the basis of information obtained by the sensor 28.

On the other hand, the control section 4 is composed of: an input/output unit 34 to which information is input by an operator and which informs the operator of treatment conditions; and the above-described main control unit 16 which constitutes the center of this system and both controls and manages input/output devices in accordance with programs and data respectively stored in program and data memory devices.

The main control unit 16 is arranged such that three systems of information about the three patients are input to and output from the main control unit 16. Since the three systems of information are input and output while being successively interchanged with each other by a multiplexer provided in the main control unit 16, it is possible for a single A/D converter and a single D/A converter (which are not shown) to process input and output information, respectively.

More specifically, the main control, unit 16 is fed with information obtained by the respective sensors 28 for the three patients via the A/D converter while successively interchanging the information by means of the multiplexer. On the basis of the thus input information and the information which is delivered from the input/output unit 34 by the operator, the main control unit 16 controls the output of each magnetron 8 by outputting information via the D/A converter while successively interchanging the output information by means of the multiplexer so that the temperature of cancerous cells (referred to simply as the "internal temperature", hereinafter) inside each body 26 is maintained at a desired value. In addition, the main control unit 16 delivers the various above-described information to the input/output unit 34 in order to apprise the operator of the heating conditions of each body 26.

The general operation of the above-described heating apparatus will be described hereinunder with reference to FIGS. 3 to 5. It is to be noted that, in the following description, a target value for the temperature of the surface of each body 26 (referred to simply as the "surface temperature", hereinafter) whic contacts the corresponding applicator 18 is set at 20° C., while a target value for the internal temperature is set at 43.5° C.

Figure 3:
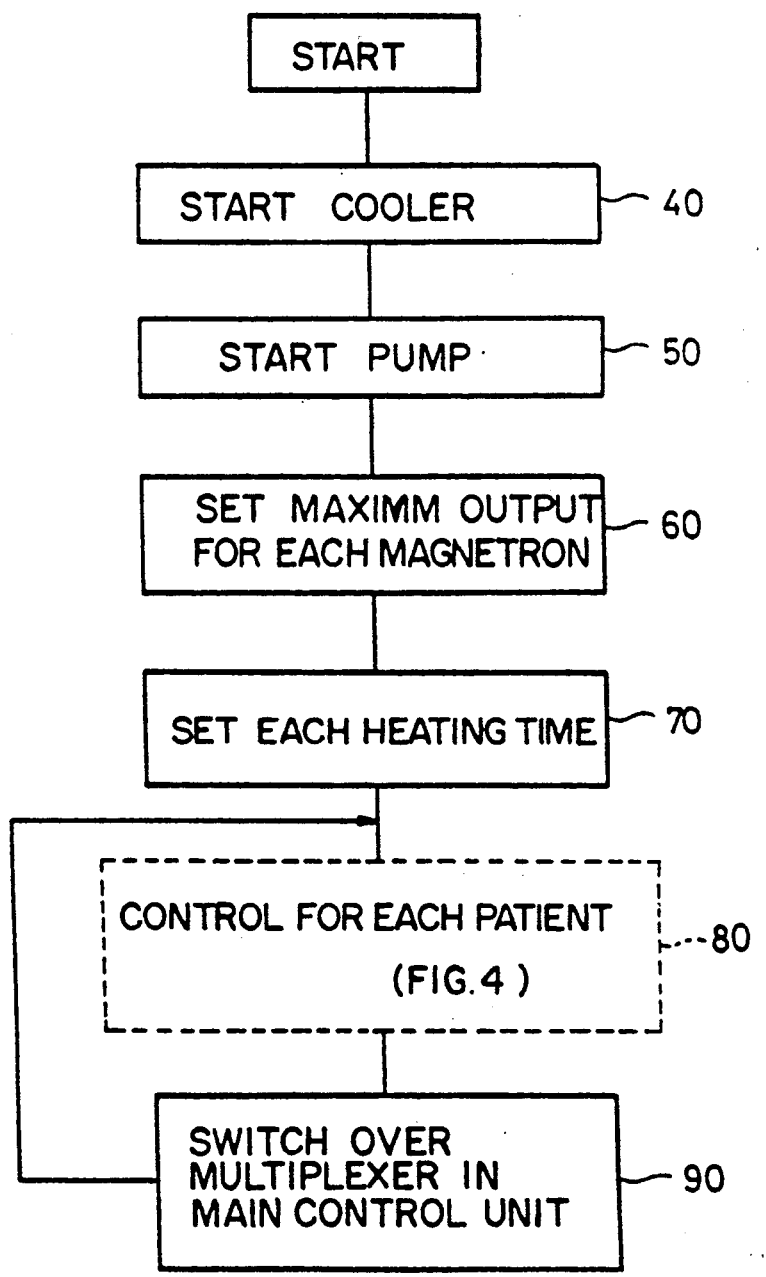
FIGS. 3 and 4 are flow charts which show the operation of the embodiment illustrated in FIG. 1.

First, the cooler 20 is started (Step 40 shown in FIG. 3), and after the water has been sufficiently cooled, the pump 22 is started (Step 50 in FIG. 3). Then, the operator predetermines a maximum output level for each magnetron 8 in accordance with the depth below the skin of the cancerous cells in the body of each patient and sets the level from the input/output unit 34 (Step 60 in FIG. 3). Then, the operator predetermines a maximum output level for each magnetron 8 in accordance with the depth below the skin of the cancerous cells in the body of each patient and sets the level from the input/output unit 34 (Step 60 in FIG. 3).

Figure 6:
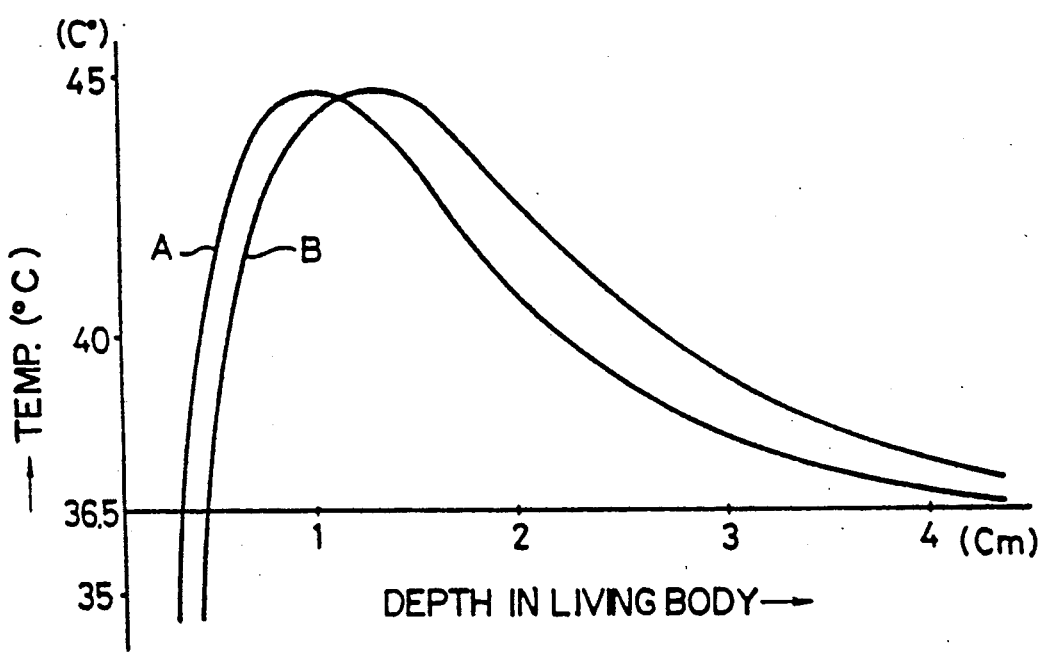
FIGS. 6 and 7 are graphs which show temperature distribution with respect to depth below the skin of a living body.
Figure 7:
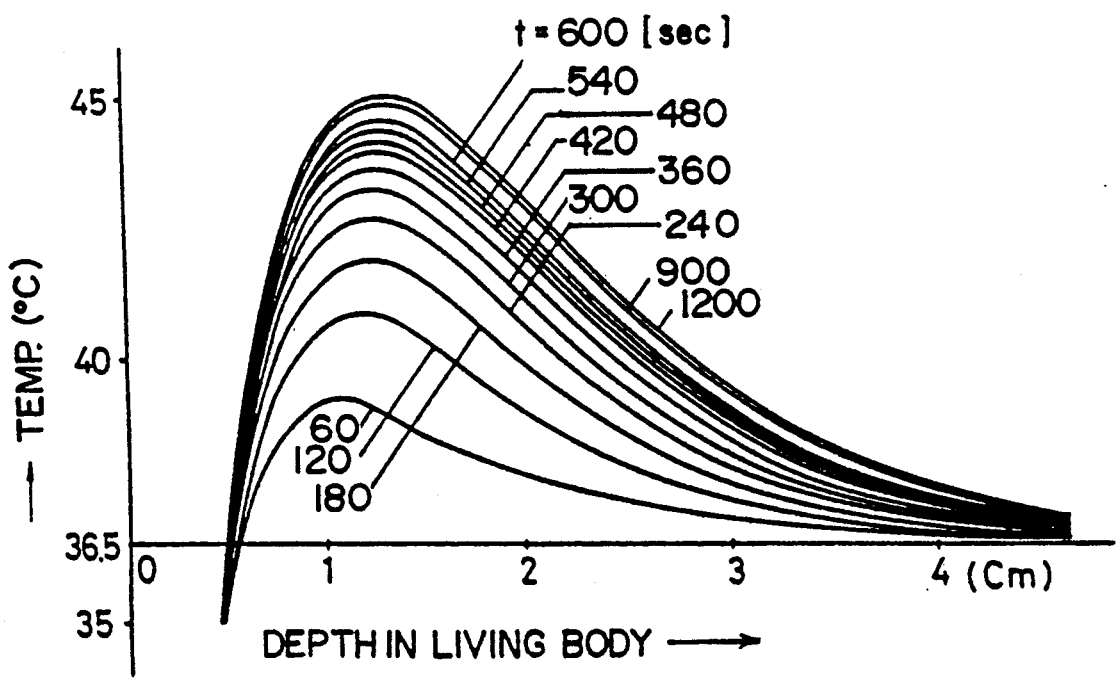

The reason why a maximum output of each magnetron 8 is set in accordance with the depth of the cancerous cells is as follows. As the microwave output is increased the temperature peak in heating is shifted toward the surface of a body, whereas as the microwave output is decreased the temperature peak is shifted toward the inside of the body since in such a case the heat gradually penetrates into the body. For this reason, it is necessary for a maximum output of each magnetron 8 to be set at a value which fits the condition of the corresponding patient. FIG. 6 is a graph which represents the results of experiments carried out on a phantom model which approximated to a living body. The graph shows comparison between a temperature distribution (A) obtained by irradiating the phantom model with a microwave of 2,450 MHz on the basis of a reference quantity, and a temperature distribution (B) obtained by irradiating the phantom model with a microwave whose output was set by subtracting 3 dB from that reference quantity. Such a frequency band is highest in the frequency regions for hyperthermia, and consequently, the range of temperature peaks is limited to the surface layer of the phantom mode. It may nevertheless be understood that the temperature distribution (B) has a temperature peak at a portion which is about 0.25 cm deeper than that of the temperature distribution (A). However, a reduction in the microwave output requires a correspondingly increased time to heat cancerous cells up to a target temperature. FIG. 7 is a graph which shows changes in temperature of a heated portion measured for each predetermined period of time. The curves in the graph represent heating characteristics in this embodiment.

Setting of a maximum output for each magnetron 8 in operation is effected by the main control unit 16 on the basis of information delivered from the corresponding directional coupler 10. More specifically, the main control unit 16 obtains an effective microwave output which is to be supplied to each applicator 18 in accordance with the difference between the respective power levels of the incident and reflected waves detected by the corresponding directional coupler 10. The main control unit 16 then matches the thus obtained microwave output with a value which is set by the operator from the input/output unit 34, thereby setting an optimal maximum microwave output. In this case, however, a maximum microwave output may previously be set at a predetermined level by employing a phantom model. Maximum microwave outputs for the three patients are herein represented by $P_1$, $P_2$ and $P_3$, respectively.

Next, the operator sets a heating time for each of the patients (Step 70 in FIG. 3). The reason why a heating time is set for each individual patient is that it is necessary for each treating time to be determined in accordance with the actual condition of the patient concerned.

After these initial values have been set as described above, each patient is subjected to microwave irradiation (Steps 80 and 90 in FIG. 3). A detailed flow chart for this microwave irradiation is shown in FIG. 4.

Figure 4:
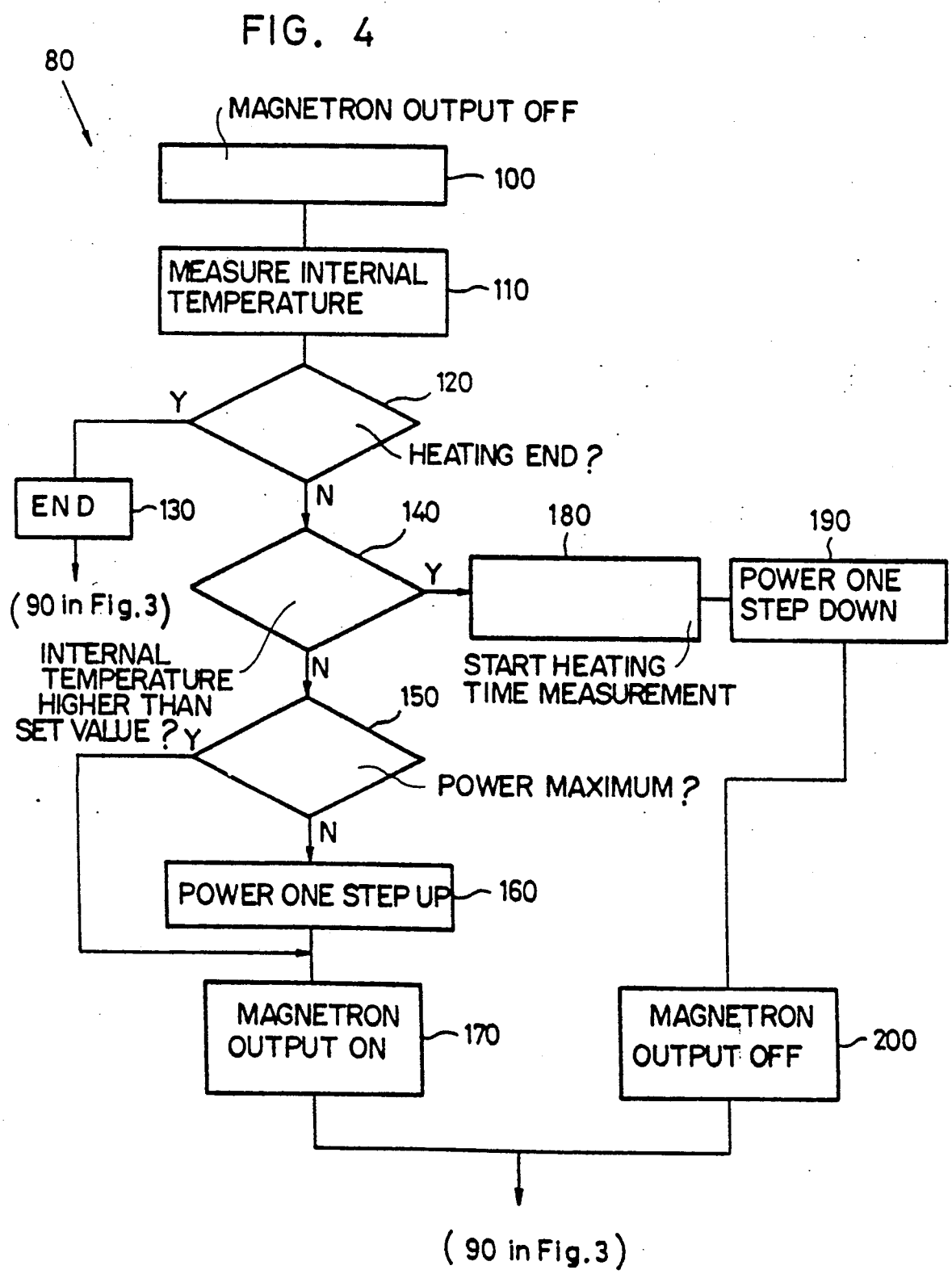

The control program shown in FIG. 4 is executed by time-division multiplexing in synchronism with clock pulses (shown in FIG. 5) generated in the main control unit 16.

Figure 5:
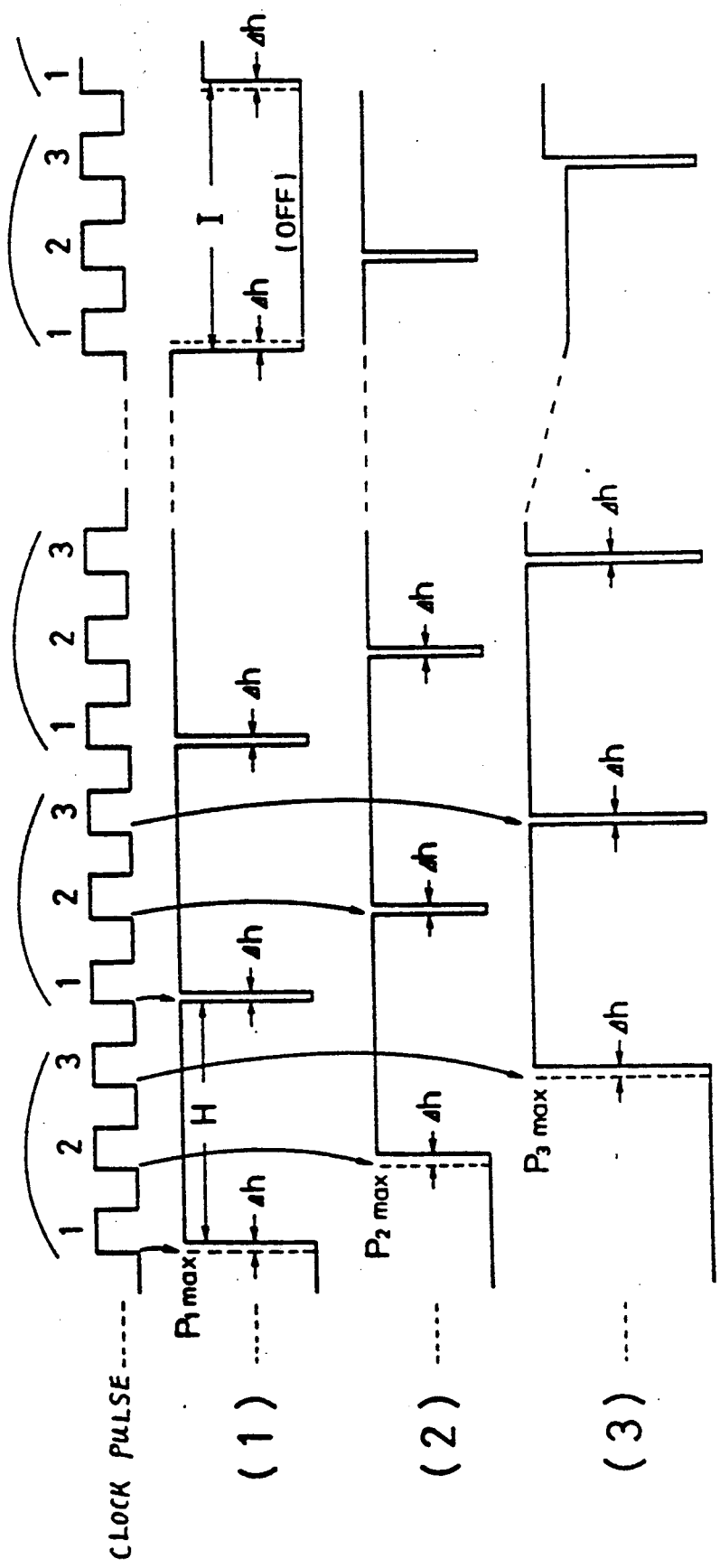
FIG. 5 is a timing chart which shows one example of the time-division multiplexing employed in the invention.

More specifically, when a clock pulse (e.g., 1) is input, the control program shown in FIG. 4 is processed within a very short period of time, that is, $\Delta h$ shown in FIG. 5, and magnetron output for each microwave irradiation period is thereby determined by a judgement made by the main control unit 16 which functions in accordance with the control program. After microwave irradiation has been effected with the thus determined magnetron output for a predetermined period of time (e.g., H in FIG. 5) (there are, as a matter of course, cases where the judgement made by the main control unit 16 is that no microwave irradiation is to be carried out), the processing of the control program is executed again in synchronism with a subsequent clock pulse 1. Thus, treatment for a single patient is carried out through a series of processings in this way. As regards the other two patients, the control program is processed in synchronism with a clock pulse 2 or 3. Thus, it is possible for a plurality of terminal devices to be controlled by a single control unit, and even a plurality of patients can be subjected to hyperthermia treatment at substantially the same time and in parallel with each other.

The flow chart shown in FIG. 4 will now be described in detail. When a clock pulse (e.g., 1) is input, the output of the magnetron 8 for a first patient is cut off in order to measure the internal temperature of this patient (Steps 100 and 110 in FIG. 4). No microwave irradiation is carried out during the measurement of internal temperature. This is because if microwave irradiation is continued, the internal temperature sensor 28 inserted into the body of the patient is affected by the microwave, which fact leads to errors in measurement of the internal temperature. After the internal temperature has been measured, a judgement is made (Step 120 in FIG. 40) as to whether or not the heating time has reached the value previously set (see Step 70 in FIG. 3). If YES, the treatment for the first patient alone is ended, and the process shifts to steps for treating the other patients (Step 130 in FIG. 4; Step 90 in FIG. 3). More specifically, the multiplexer in the main control unit 16 is switched over, and input/output ports of the main control unit 16 are changed over to the internal temperature sensors 28 and the power control units 14 for the other patients (Step 90 in FIG. 3), thus executing processing for the other patients.

If the judgement (Step 120 in FIG. 4) indicates that the heating time has not yet reached the set value, a judgement is made (Step 140 in FIG. 4) as to whether or not the internal temperature (the temperature of cancerous cells) measured beforehand is higher than the set value (43.5° C.) which has previously been input by the operator. When the internal temperature is lower than the set value, the main control unit 16 gives instructions to the power control unit 14 concerned whereby the output setting for the corresponding magnetron 8 is stepped up by one degree. However, the arrangement is such that, even when this control process is repeated for each clock pulse, the initially set maximum input power is not exceeded (see Steps 150 and 160 in FIG. 4). On the basis of this newly set value, microwave irradiation is effected (Step 170 in FIG. 4), and heating for hyperthermia is continued until a subsequent clock pulse 1 occurs. More specifically, the microwave irradiation and the measurement of internal temperature are repeated until the internal temperature becomes higher than the set value, and the output setting value for the magnetron 8 is stepped up by one degree every time this control process is executed utilizing the period of time during which the internal temperature is measured in synchronism with the clock pulse. In consequence, subsequent microwave irradiation is effected on the basis of the stepped-up output setting value.

On the other hand, when the judgement (Step 180 in FIG. 4) indicates that the internal temperature becomes higher than the set value as a result of the above-described microwave irradiation, measurement of the heating time is immediately started by the main control unit 16 (Step 180 in FIG. 4). At this time, since the internal temperature (the temperature of cancerous cells) is slightly higher than the set value, the output setting value for the magnetron 8 is stepped down by one degree for the purposes of heating in a subsequent period (Step 180 in FIG. 4). The output of the magnetron 8 is continuously cut off until a subsequent clock pulse 1 occurs (Step 200 in FIG. 4), and if the internal temperature is judged to be lower than the set value in the control process subsequently repeated, the output of the magnetron 8 is turned on through the aforementioned Steps 160 and 170 (see FIG. 4). This repetition of the control process is effected within a very short period of time by the above-described time-division multiplexing, whereby a highly accurate heating for hyperthermia is continued over a long period of time, as shown in FIG. 8 which will be described later.

In this case, the main control unit 16 is programmed such that, when repeating the control program shown in FIG. 4, the main control unit 16 actually executes only those steps which need to be executed for each repetition of the control program. For example, a program is arranged such that a first control is executed from Step 170 in FIG. 4 "Output of Magnetron 8 ON (at a maximum output, in this case)", and if Step 180 in FIG. 4 "Start Heating Time Measurement" is once executed, this Step 180 is skipped in the control effected thereafter. In addition, when treatment for all the patients has been completed, a display lamp (not shown) is turned on, and the drive of the apparatus is suspended by the operator.

Figure 8:
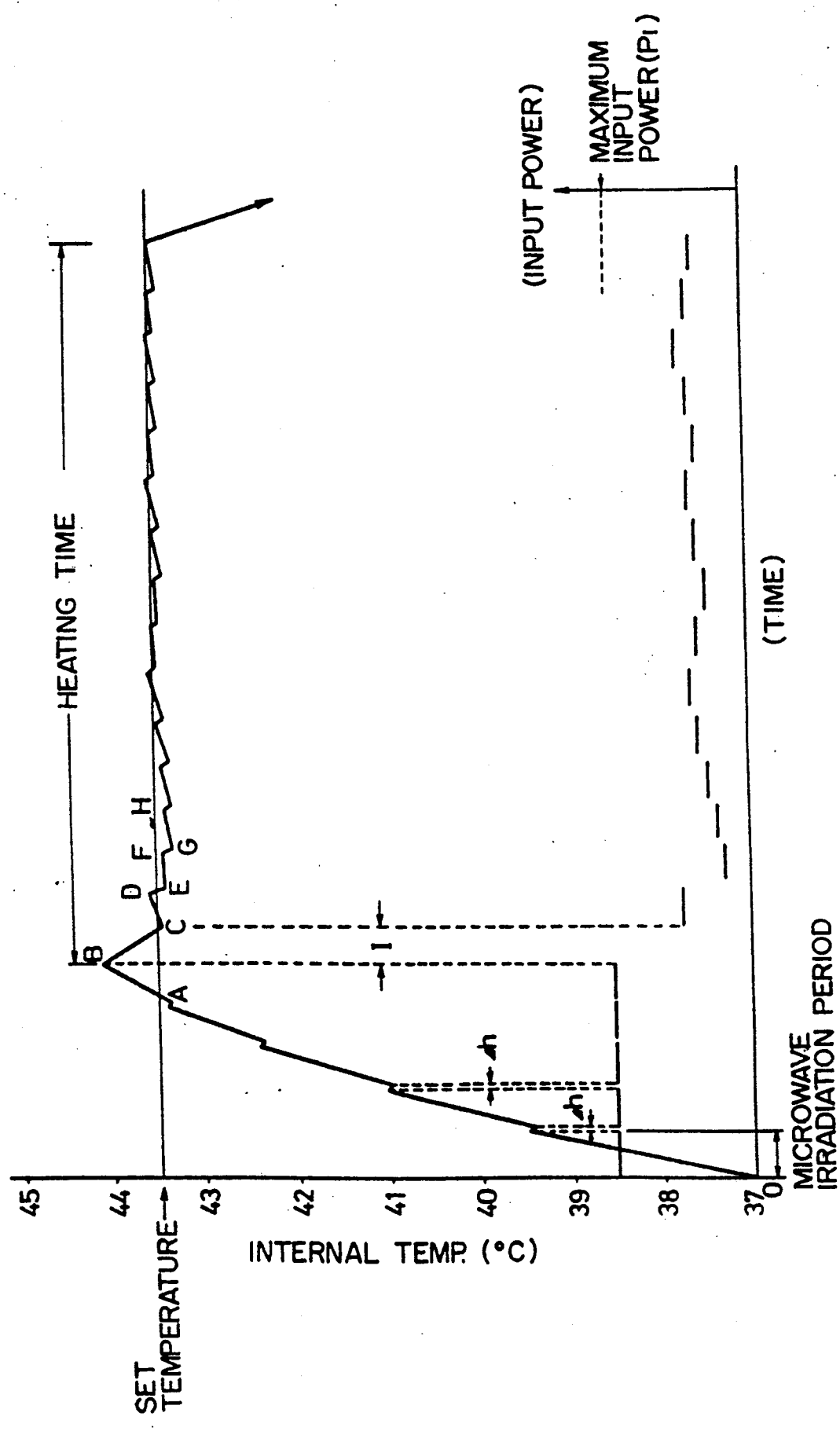
FIGS. 8 and 9 are graphs which show the action and operation of the embodiment illustrated in FIG. 1.

FIG. 8 shows changes with time in the internal temperature (the temperature of cancerous cells) of a single patient measured during each microwave irradiation period, each non-irradiation period and each internal temperature measuring period (during which the control program shown in FIG. 4 is processed), together with changes in the output of the associated magnetron 8.

In FIG. 8, each of the intervals in which the internal temperature curve ascends corresponds to a microwave irradiation period, while each of the intervals Δh in which the temperature curve descends corresponds to a period during which an internal temperature measuring operation is effected in synchronism with one clock pulse as shown in FIG. 5. During each of the internal temperature measuring periods, the output of the magnetron 8 is zero (see Step 100 in FIG. 4). The point B in FIG. 8 represents a point of time at which the internal temperature first exceeds the set value as the result of the microwave irradiation by a maximum output ($P_1$) of the magnetron 8 and the measurement of the heating time is hence started. The above-described heating time is counted from this point B. The length of the period of time after the internal temperature has reached 43° C. or thereabouts is one of the primary factors used in reaching a decision as to whether or not it is possible to effectively liquidate cancerous cells. For this reason, the heating time is set in accordance with the particular condition of each patient (Step 70 in FIG. 3).

Thereafter, instructions are continuously given to cut off the output of the magnetron 8 during each internal temperature measuring period until the internal temperature reaches 43.5° C. or below (see Steps 100 and 200 in FIG. 4). During this period (the period between B and C in FIG. 8), the output of the magnetron 8 which is to be applied subsequently is newly set, and at the point of time when the internal temperature reaches 43.5° C. or below, microwave irradiation is resumed (during the period between C and D in FIG. 8). The time I between B and C corresponds to, for example, the time I which is shown in FIG. 5. During the period between C and D in FIG. 8, the internal temperature curve is smaller in terms of the degree of slope than that between A and B since the output setting value for the magnetron 8 has been lowered.

In the case where the internal temperature does not reach 43.5° C. in the next microwave irradiation (e.g., during the period between E and F in FIG. 8) since the output setting value for the magnetron 8 has been excessively lowered during an internal temperature measuring period, the magnetron output is stepped up during the next internal temperature measuring period (e.g., the period between F and G in FIG. 8) as shown in Step 160 in the flow chart of FIG. 4. In consequence, the degree of slope of the internal temperature curve is increased again (during the period between G and H in FIG. 8). By virtue of such repetition of control, it is possible to obtain an internal temperature control which involves substantially no ripple in heating for each of the patients. Since an internal temperature above 45° C. adversely affects normal cells, it is necessary for the maximum output of the magnetron 8 and the irradiation time to be set such that the internal temperature does not exceed 45° C. at any time during the heating treatment.

Figure 9:
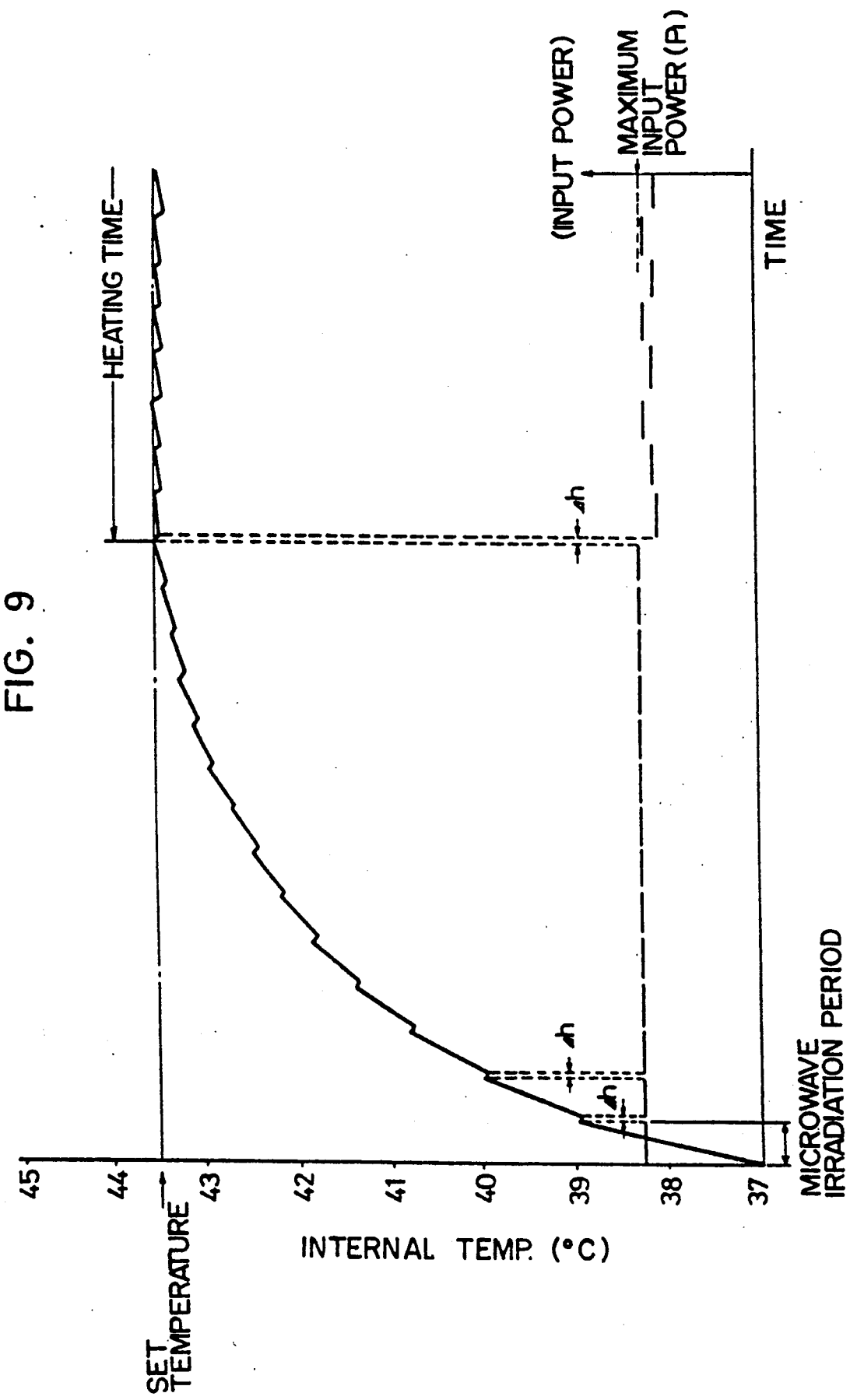

FIG. 9 shows changes in the internal temperature with time in the case wherein the maximum output of the magnetron 8 is set at a relatively low value ($P_2$) since targeted cancerous cells are present in a relatively deep part of the body of the patient.

As has been described above, it is possible according to the first embodiment to effect a highly accurate control such that the internal temperature is maintained at a set value or at values in close proximity to it over a long period of time, and it is possible for a plurality of patients to be subjected to hyperthermia treatment at the same time and in parallel with each other, which fact advantageously leads to a further increase in treatment efficiency. Since in this case a single main control unit is conveniently used in common, it is favorably possible to reduce the cost of installing treatment equipment as well as to permit a batch-type control from the center of the hyperthermia system, thus improving the controllability. Moreover, when a plurality of patients are simultaneously subjected to hyperthermia treatment, control is effectively executed for each individual patient. It is therefore advantageously possible for various patients to be individually subjected to treatments which are individually suitable even when the conditions of these patients differ from one another, for example, one for which the internal temperature curve shown in FIG. 8 is fitting and another for which the internal temperature curve in FIG. 9 is fitting.

Second Embodiment

A second embodiment of the invention will now be described with reference to FIGS. 10 to 12, in which the same constituent elements as those in the first embodiment are denoted by the same reference numerals (the same is the case with each of the embodiments described hereinafter).

The feature of the second embodiment resides in the fact that the flow rate of the coolant is controlled for each of the patients in such a manner that the surface temperature (the skin temperature) of a heated region of the body of each patient is maintained in the approximate vicinity of a predetermined value and that the respective outputs of a plurality of electromagnetic wave generating means are controlled by a single main control unit while being interchanged with each other in such a manner that the outputs are controlled for individual patients, explained in detail in the description of the first embodiment. Thus, the second embodiment aims at effectively treating a plurality of patients at the same time and in parallel with each other while preventing the patients from being thermally burned.

Figure 10:
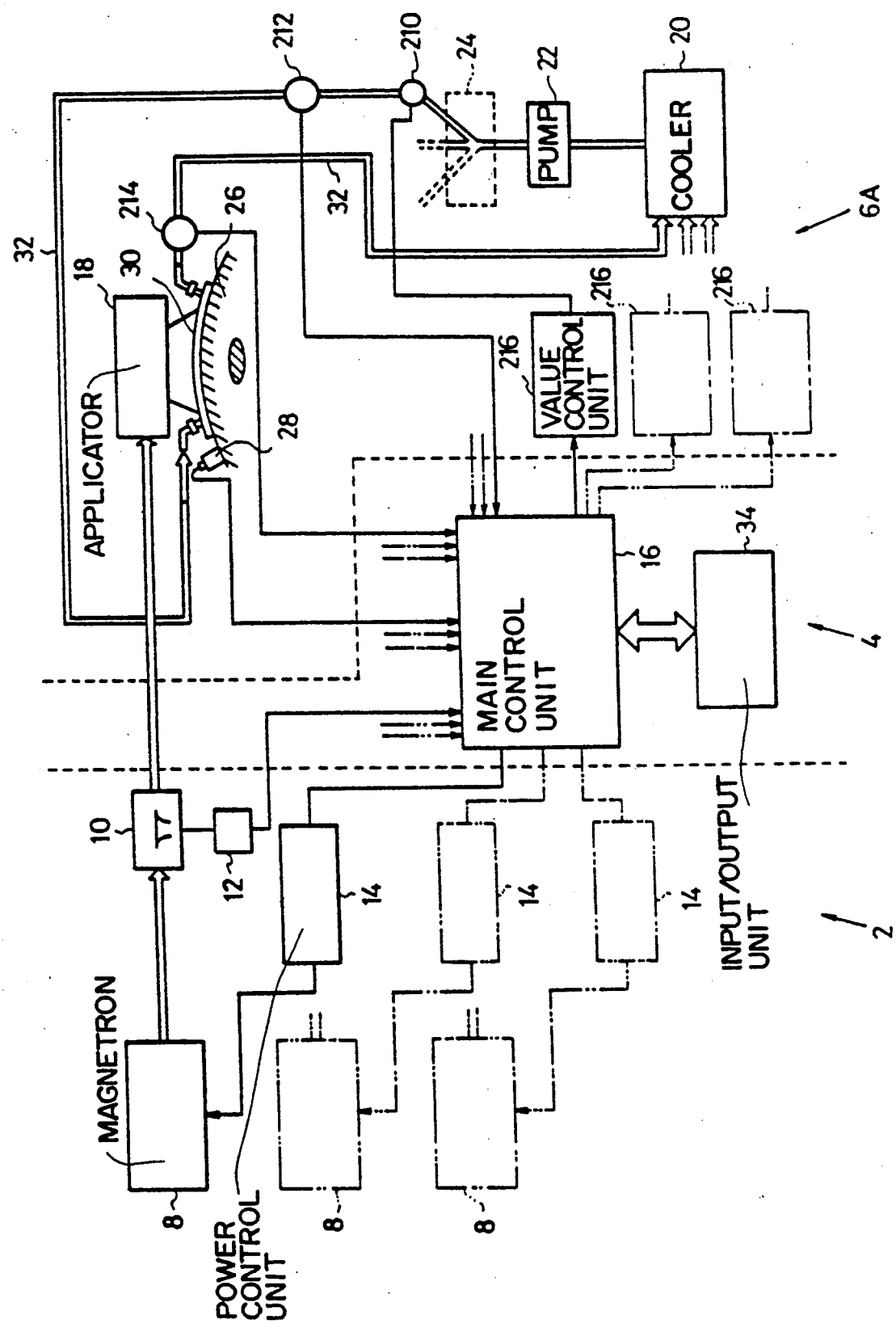
FIG. 10 is a general system diagram of a second embodiment of the invention.

To this end, each of the valves 210 and each of the flow rate sensors 212 are, as shown in FIG. 10, provided between the branching circuit 24 in the microwave irradiating section 6A and the inlet side of the cooling member 30 of each applicator 18, the valves 210 constituting respective essential portions of flow rate adjusting means which respectively adjust the flow rates of the coolant for individual patients, and the flow rate sensors 212 being adapted to detect the flow rate of the coolant for each patient. Additionally, valve control units 216 are provided for controlling the respective valves 210. Coolant temperature sensors 214 are also additionally provided on the respective outlet sides of the cooling members 30, the sensors 214 serving as coolant temperature detecting means each of which detects the temperature of the coolant which is to be supplied to each cooling member 30. Information detected by each flow rate sensor 212 and that detected by each coolant temperature sensor 214 are delivered to the main control unit 16 in the control section 4 through respective A/D converters (not shown). These pieces of information serve as principal reference values which are employed in the main control unit 16 to control each valve 210. More specifically, the degree of opening of each value 210 is determined by the main control unit 16 on the basis of the information detected by the corresponding flow rate sensor 212 and coolant temperature sensor 214 and is controlled by the corresponding valve control unit 216. In consequence, the flow rate of the coolant to be supplied to the cooling member 30 of each applicator 18 is controlled in accordance with the degree of opening of the corresponding valve 210, and the surface temperature of the body of each patient is thereby adjusted.

The arrangement of the other portion of the second embodiment is the same as that of the first embodiment.

The following is a description of the operation of the second embodiment with reference to FIGS. 11 and 12, in which steps which represent the same operations as those in the first embodiment are denoted by the same reference numerals (the same is the case with each of the embodiments described hereinafter). Setting values for a target surface temperature (20° C.) and a target internal temperature (43.5° C.) are also the same as those in the first embodiment.

Figure 11:
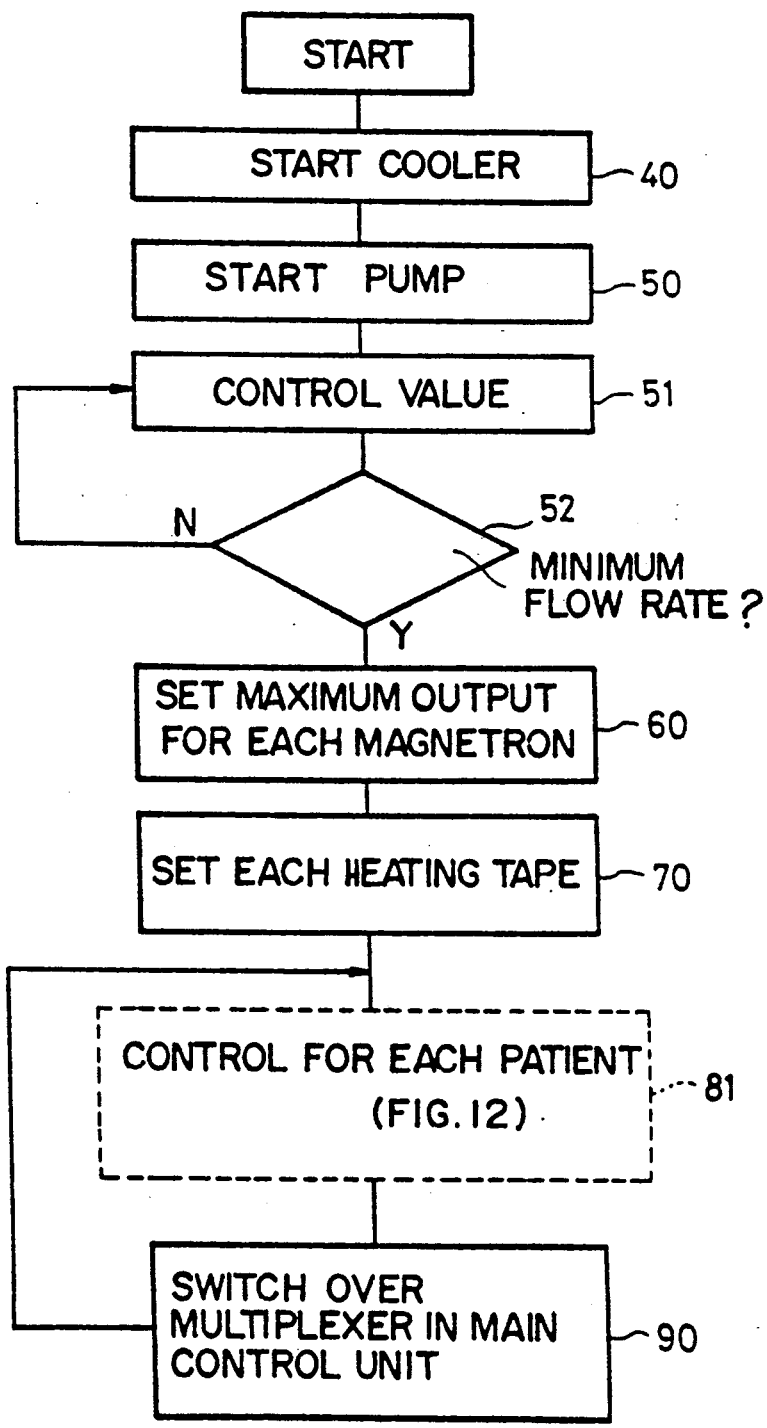

First, the cooler 20 is started (Step 40 in FIG. 11), and after the cooling water (coolant) has been sufficiently cooled, the pump 22 is started (Step 50 in FIG. 11). Then, the degree of opening of each valve 210 is controlled on the basis of the information detected by the corresponding flow rate sensor 212 such that the amount of cooling water recirculating is minimized (Steps 51 and 52 in FIG. 11). Thereafter, in a manner similar to that in the first embodiment, a maximum output of each magnetron 8 is set (Step 60 in FIG. 11), and a heating time for each patient is set by the operator (Step 70 in FIG. 11).

Then, control is effected for each patient in accordance with a flow chart shown in FIG. 12. This control is carried out in synchronism with the clock pulses shown in FIG. 5 by time-division multiplexing in a manner similar to that in the first embodiment (the same is the case with each of the embodiments described hereinafter).

when a clock pulse (e.g., 1) is input, the output of the magnetron 8 is cut off in a manner similar to that in the first embodiment for the purpose of preventing the occurrence of errors in measuring temperatures (Step 100 in FIG. 12), and the surface temperature and the internal temperature are measured (Step 111 in FIG. 12). Then, a judgement is made as to whether or not the heating time set beforehand (see Step 70 in FIG. 11) has been reached (Step 120 in FIG. 12). If YES, the treatment for the patient concerned alone is ended, and the process shifts to the control for treating another patient in a manner similar to that in the first embodiment (Step 130 in FIG. 12; Step 90 in FIG. 11). On the other hand, if the set heating time has not yet been reached, a judgement is made (Step 121 in FIG. 12) as to whether or not the surface temperature which has been previously measured is higher than the set value (20° C.) which has been input by the operator. If YES, the main control section 16 instructs the valve control unit 216 to increase the degree of opening of the valve 210 by one step in order to lower the surface temperature (Step 191 in FIG. 12), while the output of the magnetron 8 is kept cut off (Step 200 in FIG. 12). Then, the multiplexer in the main control unit 16 is switched over in such a manner that the input/output ports of the main control unit 6 are changed over for another patient (Step 90 in FIG. 11), whereby the processing for the next patient is successively executed. Then, when a subsequent clock pulse 1 is input, judgement on the surface temperature is made again (Step 121 in FIG. 12) through the above-described Steps 100, 111 and 120. If the surface temperature has lowered below the set value during a certain period of time between the processings of Step 121 in the last control process and in the present control process, the valve 210 is closed by one step so that the surface of the body of the patient is not excessively cooled (it is, however, necessary for the flow rate of water to be high enough to maintain a minimum amount of water for recirculation), and the internal temperature (the temperature of cancerous cells) is then adjusted (Steps 122 and 140 in FIG. 12).

When the internal temperature of the body of the patient is lower than the set value (43.5° C.), microwave irradiation is effected (Step 170 in FIG. 12) through Steps 150 and 160 in a manner similar to that in the first embodiment. The heating is continued until a subsequent clock pulse 1 occurs. When the internal temperature becomes higher than the set value, the measurement of heating time is started (Step 180 in FIG. 12), and microwave irradiation and the measurement of internal temperature are repeated in a manner similar to that in the first embodiment. However, if the surface temperature exceeds the set value during the repetition of the microwave irradiation and the measurement of internal temperature (Step 121 in FIG. 12), Step 191 in FIG. 12 wherein the valve 210 is opened by one step and Step 200 in FIG. 12 wherein the output of the magnetron 9 is cut off are repeatedly executed.

In the control in which the process proceeds through Steps 122, 140, 180, 190 and 191, the output of the magnetron 8 is stepped down by one degree (Step 190 in FIG. 12) and then the valve 210 is opened by one step (Step 191 in FIG. 12). This is done because it is necessary to compensate for the degree of opening of the valve 210 which has been closed by one step in Step 122 shown in FIG. 12. In other words, when the internal temperature (the temperature of cancerous cells) has become higher than the set value, it is necessary to lower the surface temperature so that the internal temperature comes close to the set value as quickly as possible.

The other operations of the second embodiment are the same as those of the first embodiment, and the heating characteristic curves respectively shown in FIGS. 8 and 9 may be applied to the second embodiment in a manner similar to that in the first embodiment.

In the second embodiment, the internal temperature and the surface temperature are respectively set at desired values for each of the patients in such a manner that the control of these temperatures is changed over from one patient to another. Accordingly, the effects offered by the second embodiment are equivalent to those offered by the first embodiment. In addition, it is possible to efficiently prevent the rise in the surface temperature of the heated region of a body. Thus, it is advantageously possible to effectively alleviate any pain, caused by, for example, thermal burn, which the patient may suffer during the hyperthermia treatment.

Third Embodiment

A third embodiment of the invention will be described hereinunder with reference to FIGS. 13 to 15.

This embodiment aims at effecting a simultaneous and parallel treatment for a plurality of patients and controlling cooling of the surface of a body at a heated region in a manner similar to that in the second embodiment. This embodiment adopts a method of cooling the surface of a body in which the temperature of a coolant (water) is controlled.

Figure 13:
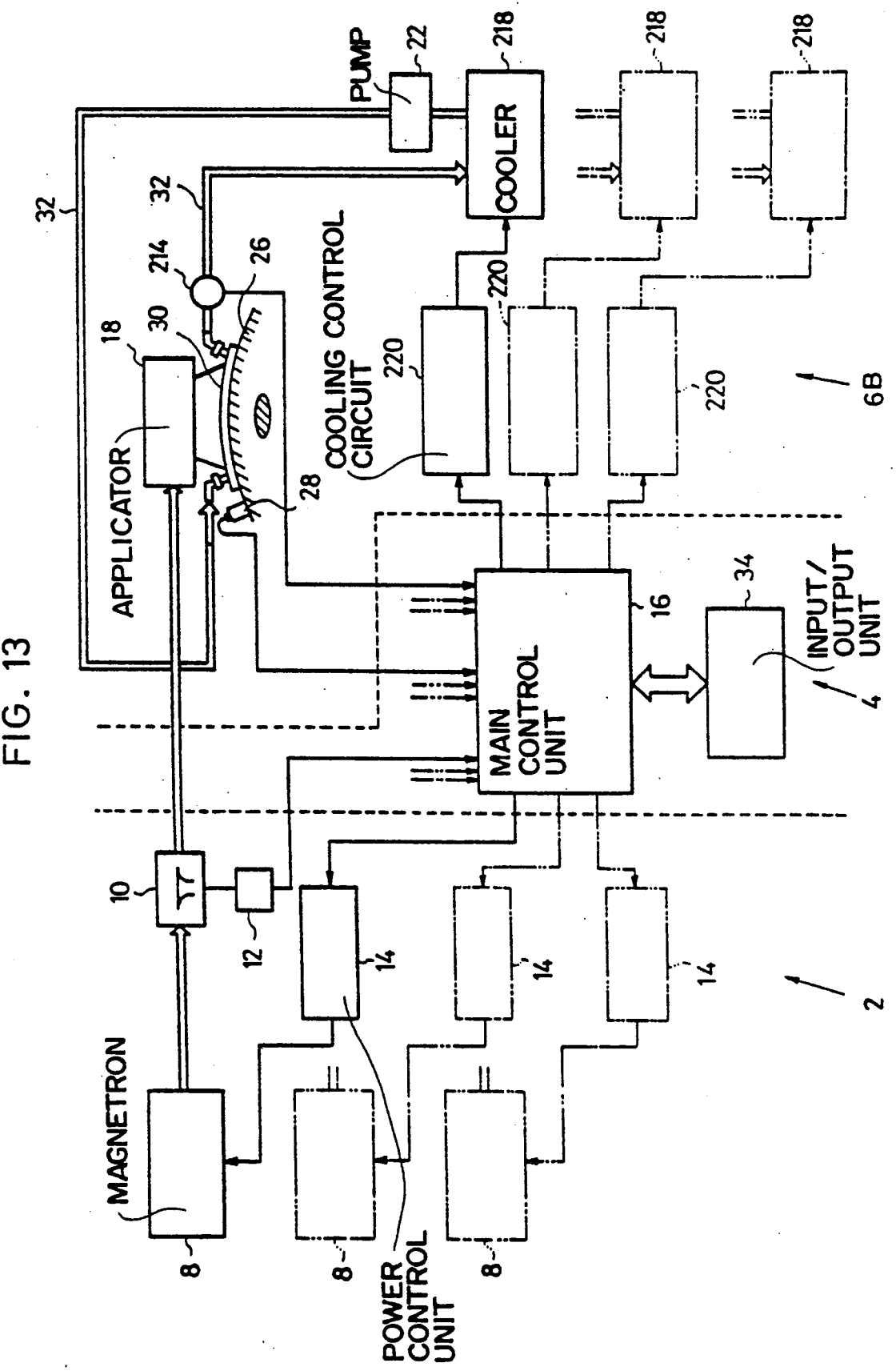
FIG. 13 is a general system diagram of a third embodiment of the invention.

More specifically, a microwave irradiating section 6B is, as shown in FIG. 13, provided with coolers 218 respectively serving as coolant cooling means each of which cools the coolant for the corresponding one of three patients, and tcooling control circuits 220 each controlling the corresponding cooler 218 thereby to adjust the temperature of the coolant. The coolant cooled in each cooler 218 is recirculated through the cooling member 30 of the applicator 18 for each patient by the operation of the corresponding pump 22. Additionally, a coolant temperature sensor 214 serving as a coolant temperature detecting means which detects the temperature of the coolant is provided on the outlet side of each cooling member 30. Temperature information detected by each coolant temperature sensor 214 is delivered to the main control unit 16 in the control section 4 as illustrated. Accordingly, the main control unit 16 obtains the surface temperature of the body 26 which is in contact with each applicator 18 on the basis of the delivered temperature information and delivers a control signal to the corresponding cooling control circuit 220 such that the surface temperature is maintained at a set value. Thus, the cooling capacity of each cooler 218 is controlled as described above.

The arrangement of the other portion of this embodiment is the same as that of the second embodiment.

The general operation and function of third embodiment will now be explained with reference to FIGS. 14 and 15. It is to be noted that the set value (43.5° C.) for the internal temperature and the set value (20° C.) for the surface temperature are the same as those in the first and second embodiments.

Figure 14:
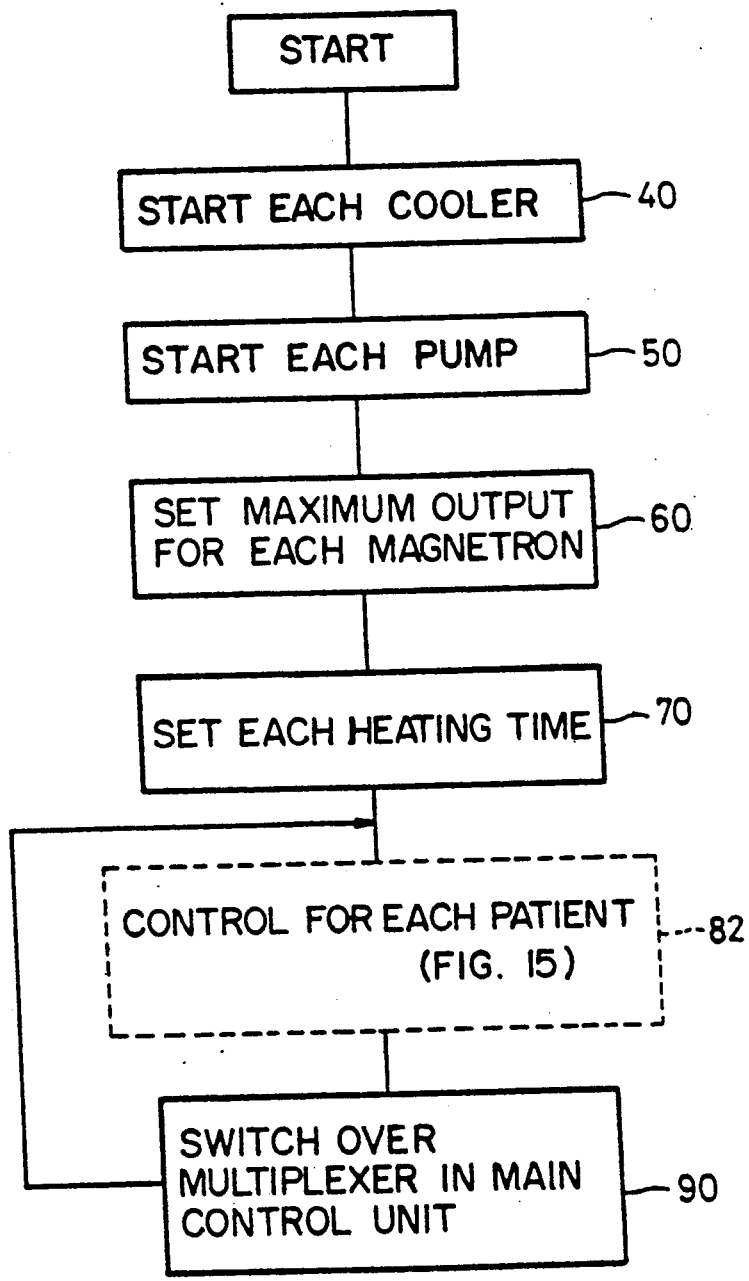
FIGS. 14 and 15 are flow charts which show the operation of the embodiment illustrated in FIG. 13.

First, each cooler 218 is started (Step 40 in FIG. 14), and after the water has been sufficiently cooled, each pump 22 is started (Step 50 in FIG. 14). Then, the operator sets a maximum output for each magnetron 8 (Step 60 in FIG. 14) and also a heating time which is matched with the condition of each patient (Step 70 in FIG. 14) from the same viewpoint as that in the first embodiment.

When the above-described initial setting has been completed, changeover control for three patients is effected by time-division multiplexing in synchronism with the clock pulses (see FIG. 5) generated in the main control unit 16 (Steps 82 and 90 in FIG. 14).

Figure 15:
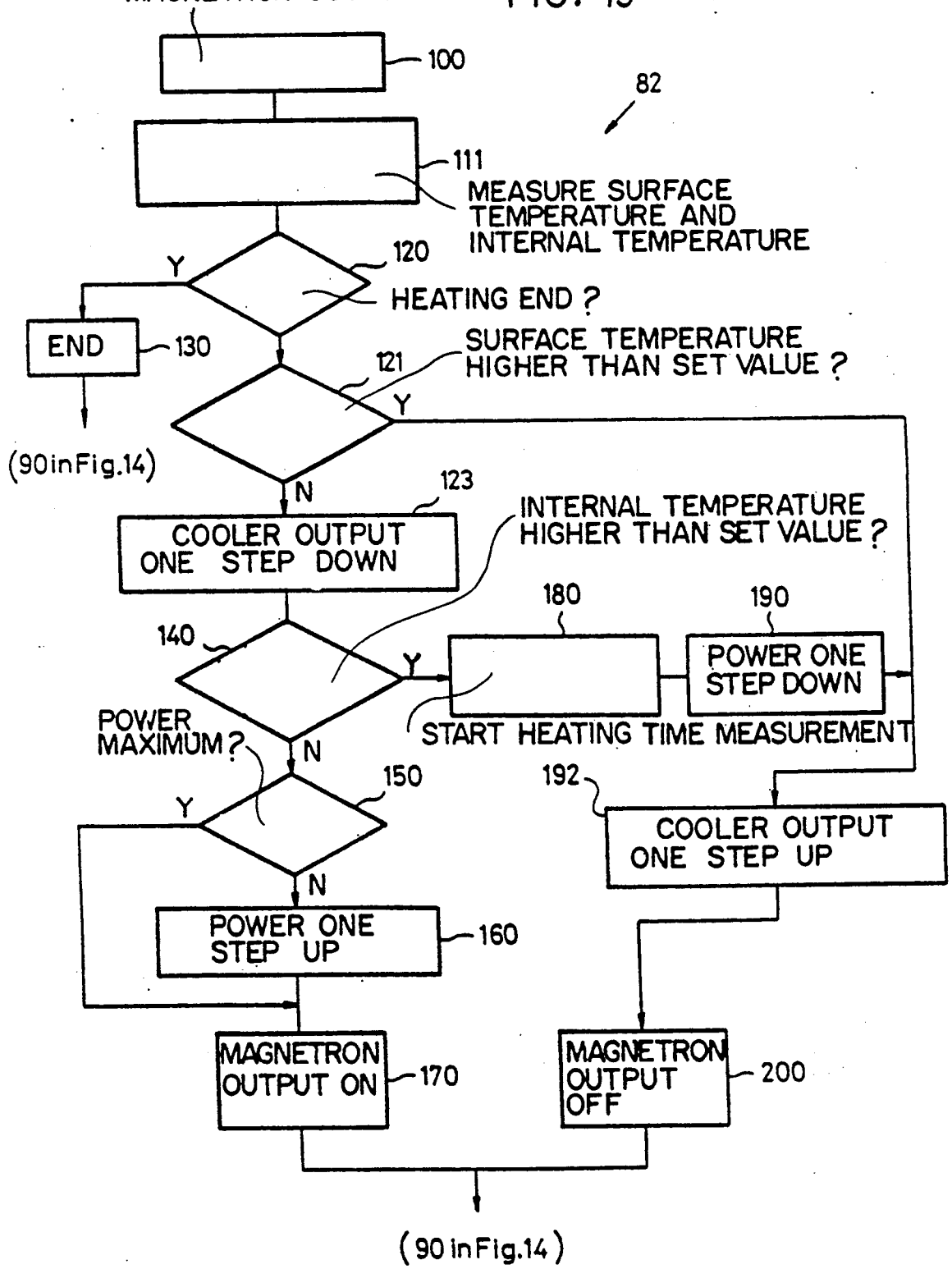

More specifically, control for each patient is carried out by the main control unit 16 in a manner such as that shown in FIG. 15. The control operation shown in FIG. 15 is generally the same as that in the second embodiment (see FIG. 12) except for the following two steps:

(1) When the surface temperature of the heated part is lower than the set value (that is, if NO is the result of the judgement made in Step 121 in FIG. 15), the output (cooling capacity) of the cooler 218 is stepped down by one degree (Step 123 in FIG. 15) in order to prevent the surface of the body of the patient from being excessively cooled (in this case, the output of the cooler 218 may be cut off, since the coolant is continuously recirculated by the pump 22 and there is therefore no fear of the surface layer of the body of the patient being thermally burned). Then, a subsequent judgement is made in Step 140.

(2) When the surface temperature is higher than the set value (that is, if YES is the result of the judgement in Step 121 in FIG. 15), the main control unit 16 instructs the output of the cooler 218 to be stepped up by one degree in order to lower the surface temperature (Step 192 in FIG. 15). Also when the measurement of heating time is started (Step 180 in FIG. 15) and the power level of the magnetron 8 is stepped done by one degree (Step 190 in FIG. 15), the output of the cooler 218 is stepped up by one degree (Step 192 in FIG. 15) in order to compensate for the cooling capacity of the cooler 218 which has been stepped down by one degree in Step 123 in FIG. 15.

Thus, in this embodiment the temperature of the coolant is employed as one of the control variables used to control the surface temperature of the heated region of the body of each patient, whereas in the second embodiment the flow rate of the coolant is employed. The heating characteristic curves respectively shown in FIGS. 8 and 9 may be also applied to this embodiment.

With the above-described arrangement, it is also possible to obtain advantageous effects which are substantially equivalent to that offered by the second embodiment. Since the coolers 218 are provided for individual patients, it is possible to effect a more precise individual control of the surface temperature. Thus, it is advantageously possible to expedite the hyperthermia treatment.

It is to be noted that this embodiment can be satisfactorily put into practical use even if the coolant temperature sensors 214 serving as coolant temperature detecting means are removed in accordance with need.

Since a relatively low frequency is employed to heat a relatively deep part of a living body, it is possible for each of the above-described embodiments to employ an oscillator which is suitable for oscillating microwaves of relatively low frequencies and a linear amplifier in place of each of the magnetrons employed in the above-described embodiments. In such a case, the power level of the oscillator is varied by employing a thyristor in a manner similar to that in the case where each magnetron is controlled by a thyristor, or by changing the amplification degree or gain of the linear amplifier. It is, however, necessary to employ an isolator for the purpose of eliminating adverse effects exerted by reflected waves.

Fourth Embodiment

A fourth embodiment of the invention will now be described with reference to FIGS. 16 to 19.

This embodiment aims at subjecting a plurality of patients to hyperthermia treatment at the same time and with high efficiency by controlling the output of each of the electromagnetic wave generating means through an ON/OFF control and controlling the flow rate of the coolant.

Figure 16:
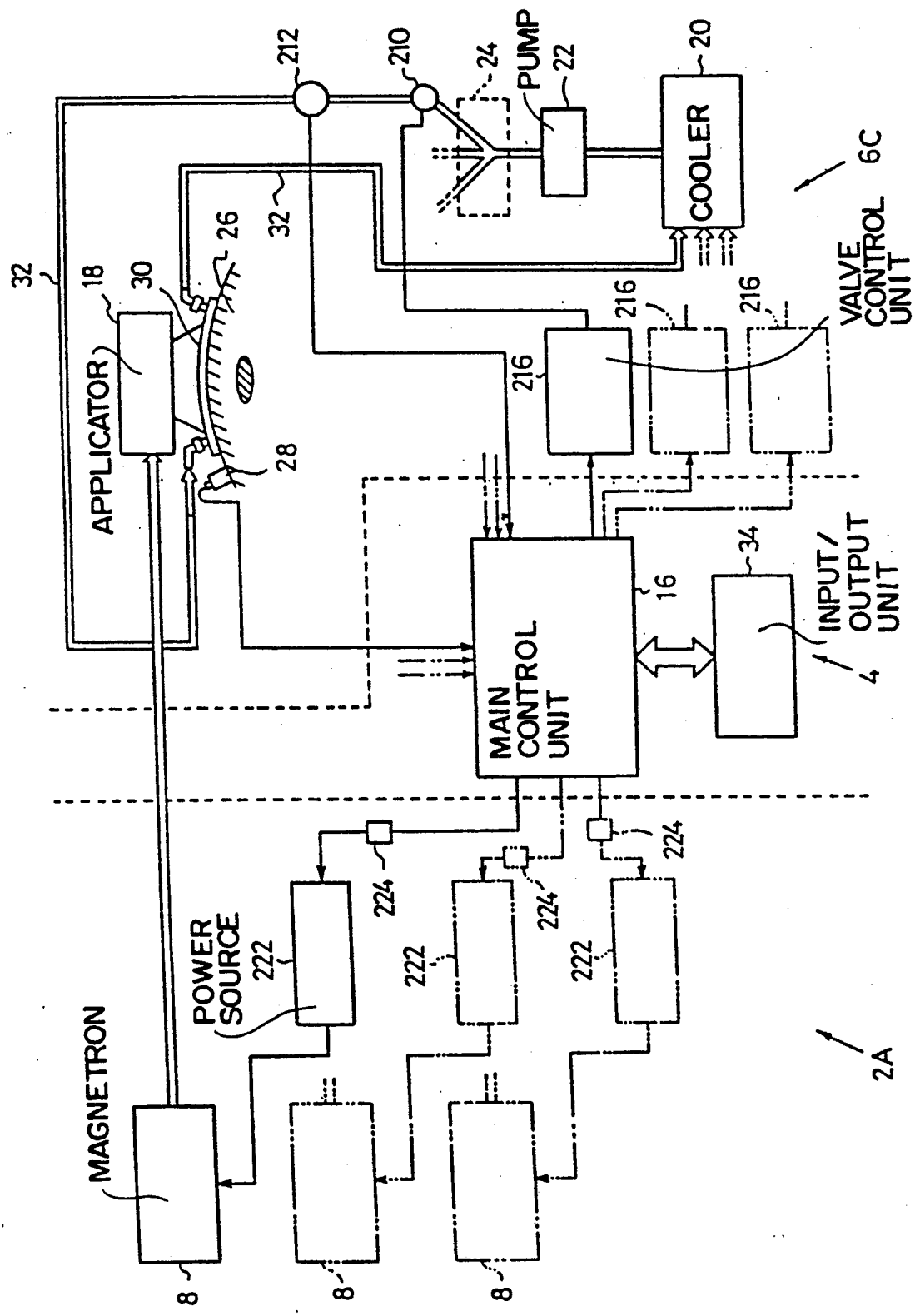
FIG. 16 is a general system diagram of a fourth embodiment of the invention.

Referring first to FIG. 16 which shows the arrangement of the fourth embodiment, a microwave generating section 2A which serves as an electromagnetic wave generating section is composed of: the magnetrons 8 respectively serving as electromagnetic wave generating means which generate electromagnetic waves for respective patients; power sources 222 each controlling the corresponding magnetron 8; and switches 224 serving as respective essential portions of ON/OFF switching means each of which ON/OFF controls the corresponding power source 222. Each switch 242 is controlled by the main control unit 16 in the control section 4 as illustrated. More specifically, the switches 224 are turned ON or OFF in accordance with predetermined instructions given from the main control unit 16, and the power sources 222 which respectively associated with the switches 224 are turned ON or OFF in response to the respective operations of the switches 224. In consequence, the magnetrons 8 are individually ON/OFF controlled.

On the other hand, information detected by each internal temperature sensor 28 and that detected by each flow rate sensor 212 are delivered to the main control unit 16 at all times. The main control unit 16 ON/OFF controls each magnetron 8 and adjusts the degree of opening of each valve 210 on the basis of the information detected and delivered thereto and instruction information input by the operator as described above.

The arrangement of the other portion of each of the main control unit 4 and the microwave irradiating section 6C is the same as that of the second embodiment. However, the temperature sensor 214 which is disposed on the outlet side of each cooling member 30 in the second embodiment is not provided in this embodiment.

Figure 17:
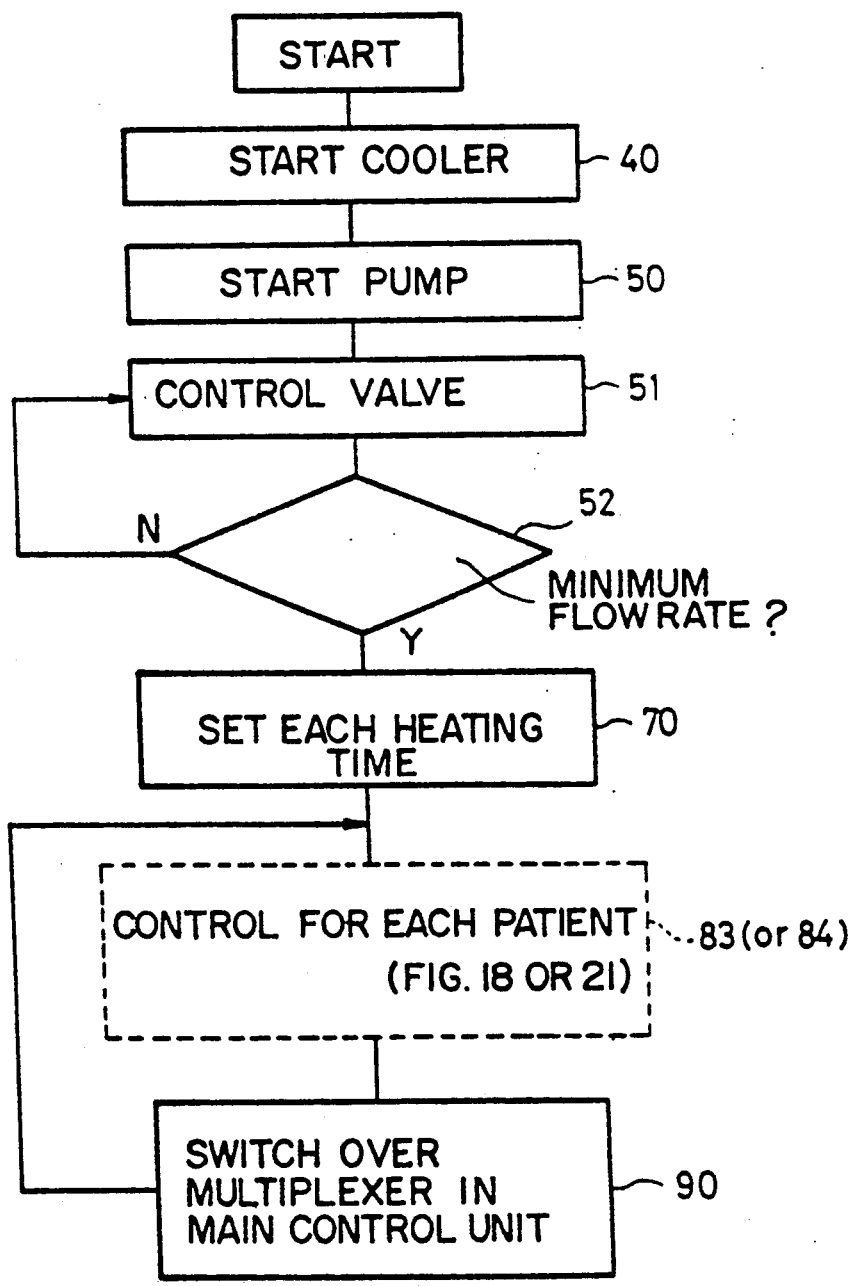
FIG. 17 is a flow chart which shows the operation of the embodiments respectively illustrated in FIGS. 16 and 20.
Figure 18:
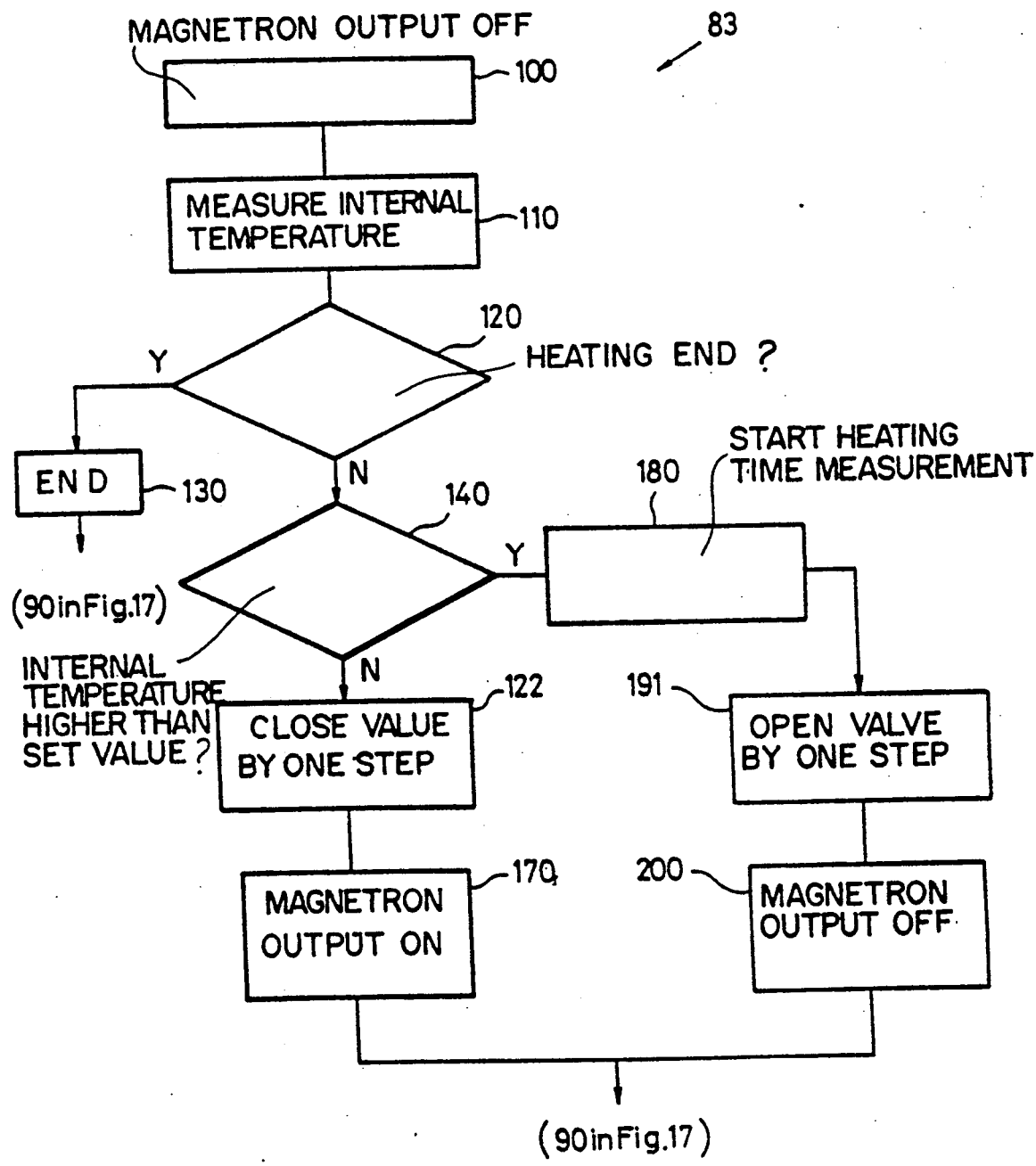
FIG. 18 is a flow chart which shows the operation of the embodiment illustrated in FIG. 16.
Figure 19:
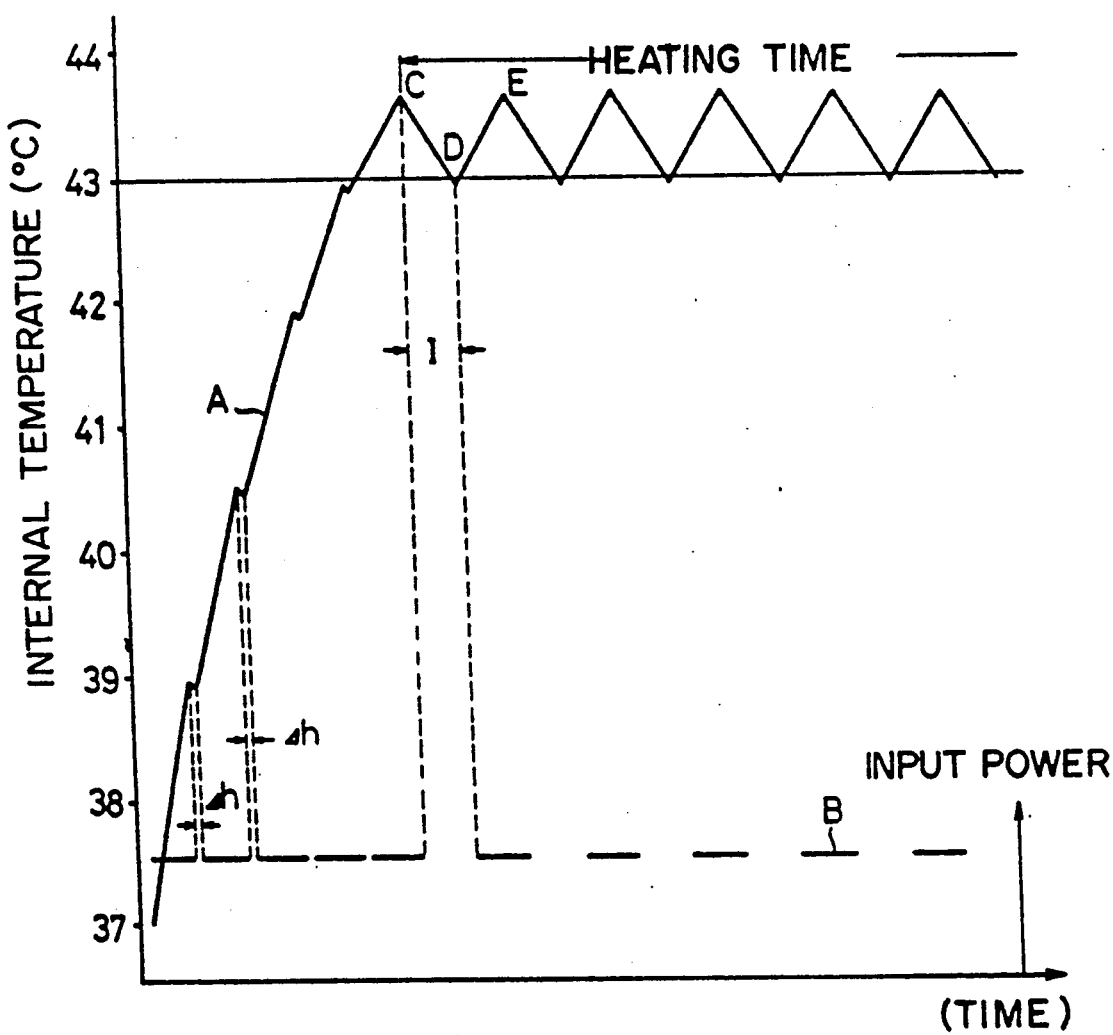
FIG. 19 is a graph which shows the action and operation of the embodiment illustrated in FIG. 16.

The following is a description of the general operation of this embodiment with reference to FIGS. 17 to 19. It is to be noted that target values for the internal temperature and the surface temperature are respectively set at 43° C. and 20° C.

First, the cooler 20 is started (Step 40 in FIG. 17), and after the cooling water has been sufficiently cooled, the pump 22 is started (Step 50 in FIG. 17). Then, the main control unit 16 controls the degree of opening of each valve 210 such that the amount of cooling water recirculating is minimized in a manner similar to that in the second embodiment (Steps 51 and in FIG. 17). In addition, a heating time which is matched with the condition of each patient is set to the main control unit 16 by the operator from the input/output unit 34 (Step 70 in FIG. 17).

After the above-described initial setting has been completed, hyperthermia treatment for three patients is started on the basis of the time-division multiplexing control effected by the main control unit in a manner similar to each of the above-described embodiments (Steps 83 and 90 in FIG. 17).

The control process for each of the three patients is shown in FIG. 18. When a clock pulse 1 shown in FIG. 5 is input, instruction is given to cut off the output of the magnetron 8 for, for example, a first patient (Step 100 in FIG. 18), and the measurement of internal temperature is effected on the basis of the information detected by the internal temperature sensor 28 (Step 110 in FIG. 18).

Then, a judgement is made as to whether or not the heating time previously set has been reached (Step 120 in FIG. 18). If YES, the hyperthermia treatment for the first patient is ended, and the process shifts to the heating control for a second patient (step 13 in FIG. 18; Step 90 in FIG. 17). However, if the judgement made in Step 120 indicates that the heating time has not yet been reached, then a judgement is made as to whether or not the internal temperature is higher than the set value (43° C.) (Step 140 in FIG. 18).

When the internal temperature (the temperature of cancerous cells) is lower than the set value, the valve 210 is closed by one step (Step 122 in FIG. 18), whereby the surface temperature is raised (however, in this case also, it is necessary for the flow rate of cooling water to be high enough to maintain a minimum amount of cooling water for recirculation in order to prevent the surface of the body of the patient from being thermally burned). This is done because it is also necessary to effect a temperature adjustment at the surface of the patient body so that the temperature of cancerous cells inside the body quickly reaches the set value. Then, the main control unit 16 instructs the output of the magnetron 8 to be turned ON (Step 170 in FIG. 18), whereby microwave irradiation is effected by a predetermined output of the magnetron 8 for a predetermined period of time (see H in FIG. 5). During this microwave irradiation period, the multiplexer is switched over to effect control similar to the above for each of the second and third patients. When a subsequent clock pulse 1 occurs, the control for the first patient is resumed.

When the internal temperature becomes higher than the set value during the repetition of a loop similar to the above (that is, if the answer of the judgement made in Step 140 in FIG. 18 is YES), the measurement of heating time is started by the main control unit 16 (Step 180 in FIG. 18), and the valve 210 is opened by one step (Step 191 in FIG. 18). Thus, the surface temperature is lowered, and the internal temperature is also thereby adjusted at the surface of the body of the patient so that the temperature of cancerous cells quickly returns to the set value. During this adjustment period, the magnetron 8 is turned OFF (Step 200 in FIG. 18), and processing for the other patients is carried out in a manner similar to the above.

The above-described control is effected for each of the patients, and heating at a temperature in the vicinity of 43° C. is started from a point of time when the internal temperature first exceeds the set value (see the point C in FIG. 19). This heating is continued until the heating time set by the operator has elapsed.

Figure 20:
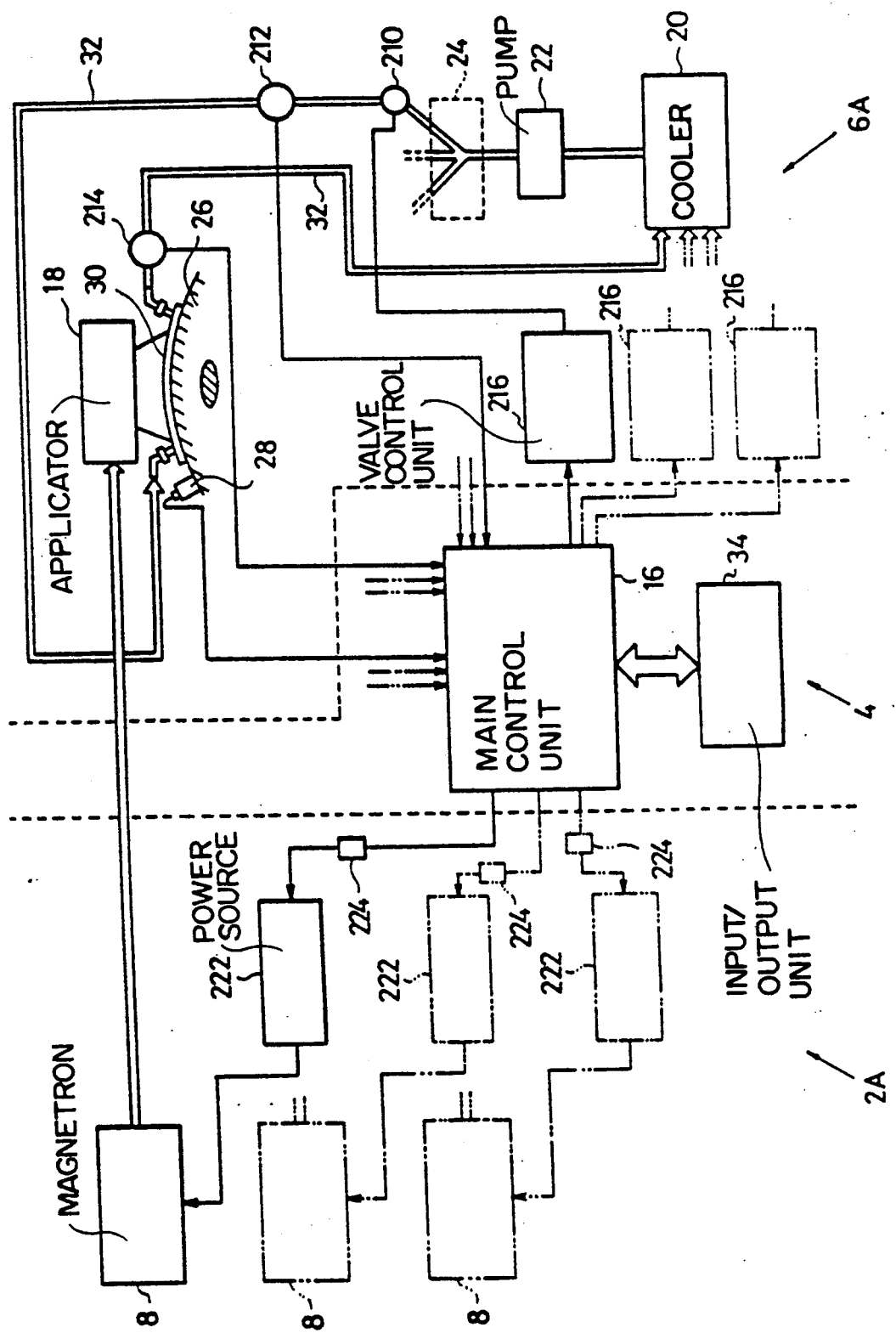
FIG. 20 is a general system diagram of a fifth embodiment of the invention.

FIG. 20 shows one example of the above-described heating characteristic curves. In this Figure, the reference symbol A represents how the internal temperature (the temperature of cells) rises, while the symbol B represents how the output of the magnetron 8 is ON/-OFF controlled (showing either one of the ON and OFF states). The point C, as described above, represents a point of time when the measurement of heating time is started in response to the detection of the fact that the internal temperature has reached the point of exceeding the set value as the result of the microwave irradiation. The section between C and D shows a change in the internal temperature when the output of the magnetron 8 is OFF, while the section D and E shows a change in the internal temperature when the output of the magnetron 8 is ON. Thus, it is possible for the internal temperature to be quickly raised to the set value. Even when the internal temperature exceeds the set value, the internal temperature can be quickly lowered, since it is possible to cool the surface of the body of the patient. Accordingly, it is advantageously possible for the internal temperature to be constantly maintained at approximately 43° C.

As has been described above, this embodiment offers advantageous effects which are substantially equivalent to those offered by the second embodiment. Since the output of each of the electromagnetic wave generating means is simply ON/OFF controlled without employing any complicated output control means, the arrangement is simplified correspondingly. Accordingly, it is advantageously possible to improve the controllability and reduce the cost of installing treatment equipment.

Fifth Embodiment

A fifth embodiment of the invention will be described hereinunder with reference to FIGS. 17 and 20 and 21.

This embodiment aims at precisely controlling also the surface temperature in addition to the object of the fourth embodiment.

To this end, a coolant temperature sensor 214 (one which is the same as that employed in the second embodiment) is additionally provided on the outlet side of the cooling member 30 of each applicator 20 as shown in FIG. 20, the sensor 214 serving as a coolant temperature detecting means which measures the temperature of cooling water. Information detected by each coolant temperature sensor 214 is delivered to the main control unit 16. The arrangement of the other portion of this embodiment is the same as that of the fourth embodiment.

Figure 21:
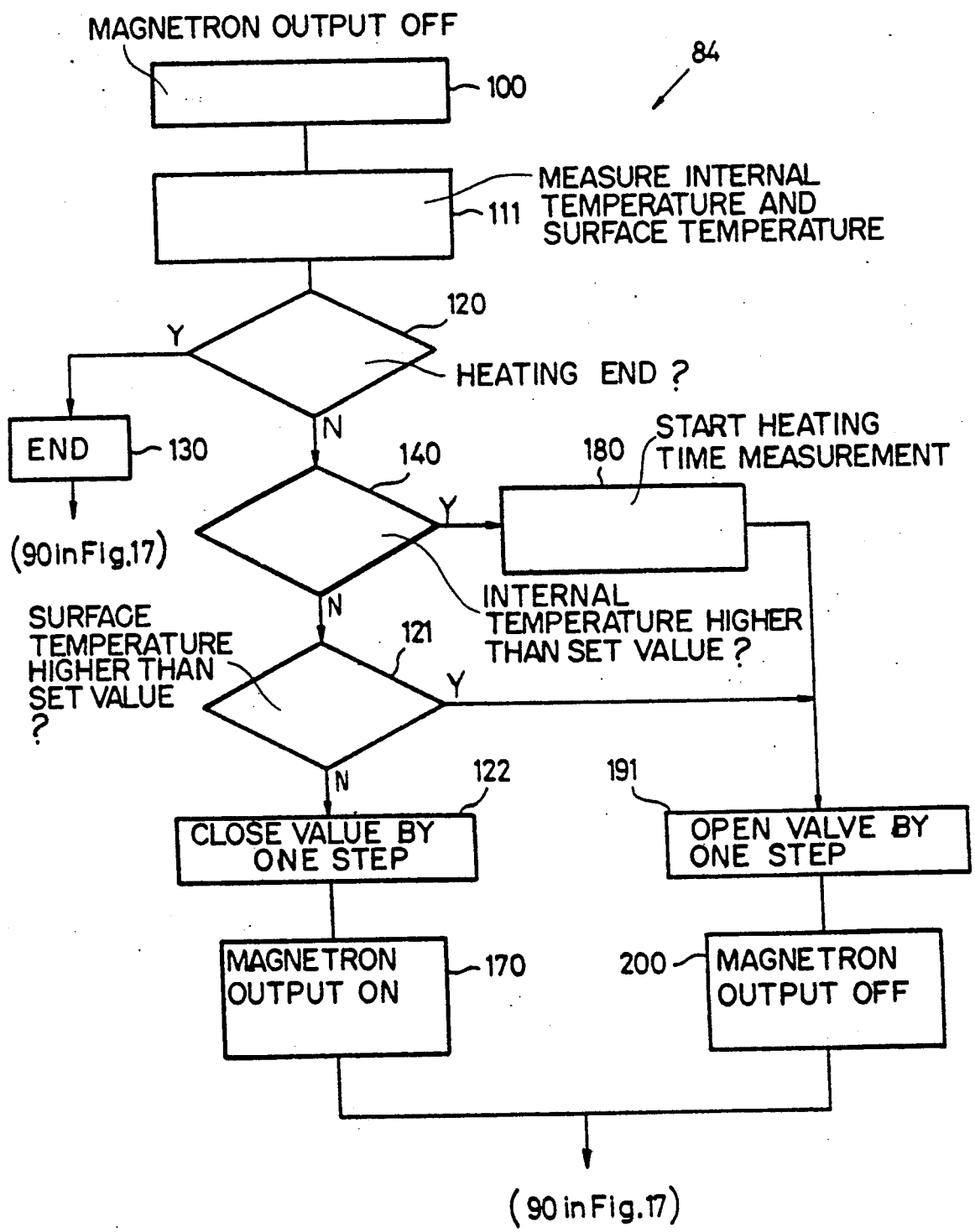
FIG. 21 is a flow chart which shows the operation of the embodiment illustrated in FIG. 20, in cooperation with the flow chart of FIG. 17.

General control of this embodiment is effected in accordance with flow charts respectively shown in FIG. 18, which shows the operation of the fourth embodiment, and FIG. 21. In this case, target values for the internal temperature and the surface temperature are respectively set at 43° C. and 20° C.

According to the above-described flow charts, the following functions are added to those of the fourth embodiment:

(1) The surface temperature of the body of each patient is measured (Step 111 in FIG. 21).

(2) A judgement is made as to whether or not the surface temperature is higher than the set value (20° C.) (Step 212 in FIG. 21), and the degree of opening of the corresponding valve 210 is adjusted by feedback control (Steps 122 and 191 in FIG. 21).

Since this embodiment is arranged and operated as described above, it is possible to obtain advantageous effects which are equivalent to those offered by the fourth embodiment. Since the surface temperature is monitored at a regular predetermined timing for effecting a precise control, it is possible for the surface temperature to be maintained at a predetermined value where the patient suffers no pain. Thus, it is advantageously possible to prevent the occurrence of any thermal burn or the like.

Sixth Embodiment

A sixth embodiment of the invention will now be described with reference to FIGS. 22 to 24.

This embodiment aims at effecting a simultaneous and parallel hyperthermia treatment for a plurality of patients by simply ON/OFF controlling the output of each of the electromagnetic wave generating means and by controlling the temperature of the coolant.

Figure 22:
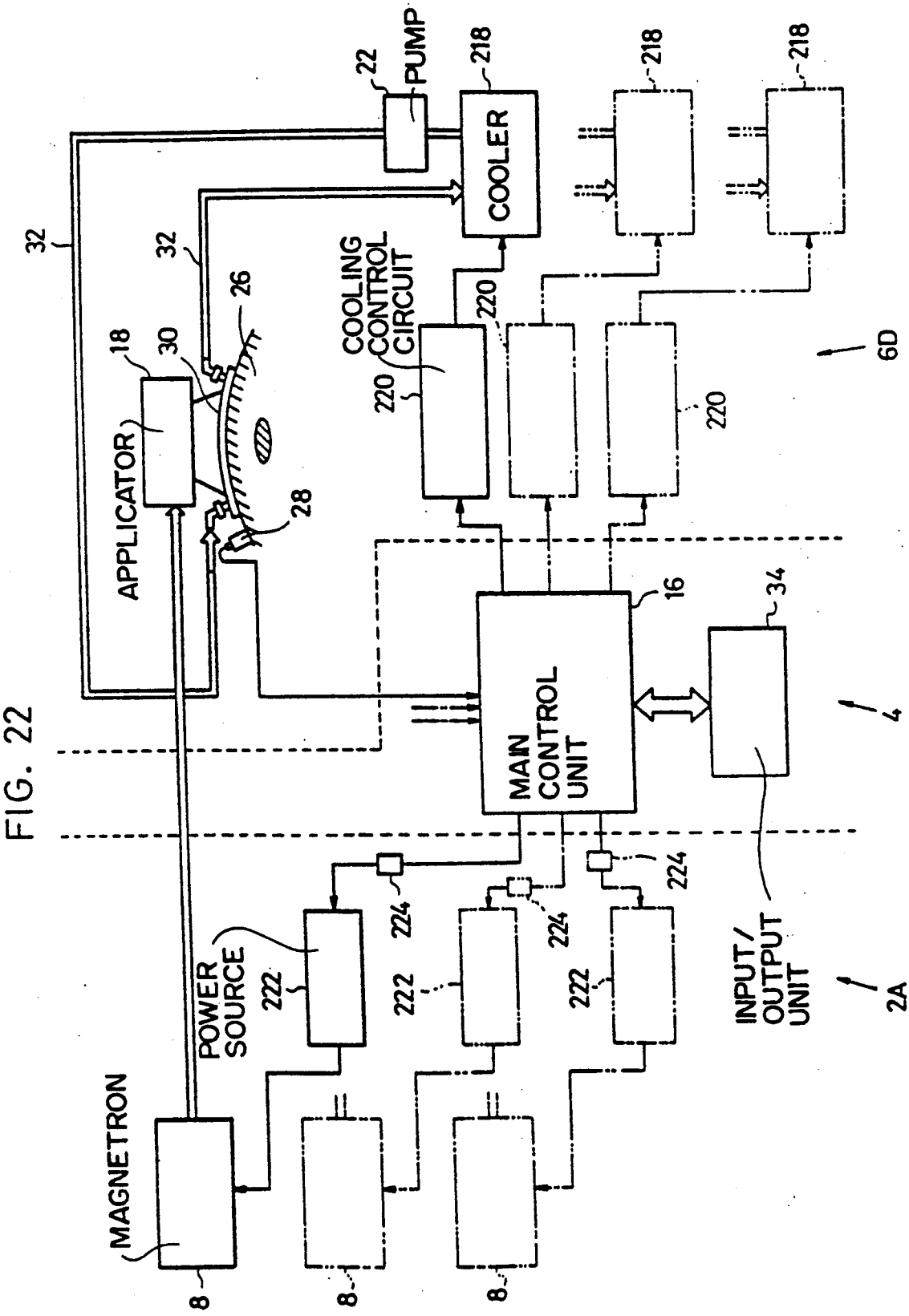
FIG. 22 is a general system diagram of a sixth embodiment of the invention.

Referring first to FIG. 22, the arrangement of this embodiment is as follows.

(1) The microwave generating section 2A has the same arrangement as that of the fifth embodiment (see FIG. 20).

(2) The microwave irradiating section 6D is arranged in a manner similar to that of the third embodiment. However, this section 6D is not provided with the coolant temperature sensors 214 (see FIG. 13).

(3) The main control unit 16 in the control section 4 is adapted to control each cooling control circuit 220 and each switch 224 on the basis of information detected by the corresponding internal temperature sensor 28 inserted into the body 26 and instructions given by the operator via the input/output unit 34.

The following is a description of the general operation of this embodiment. It is to be noted that target values for the internal temperature and the surface temperature are respectively set at 43° C. and 20° C. Steps which respectively show the same operations as those in each of the above-described embodiments are denoted by the same reference numerals.

Figure 23:
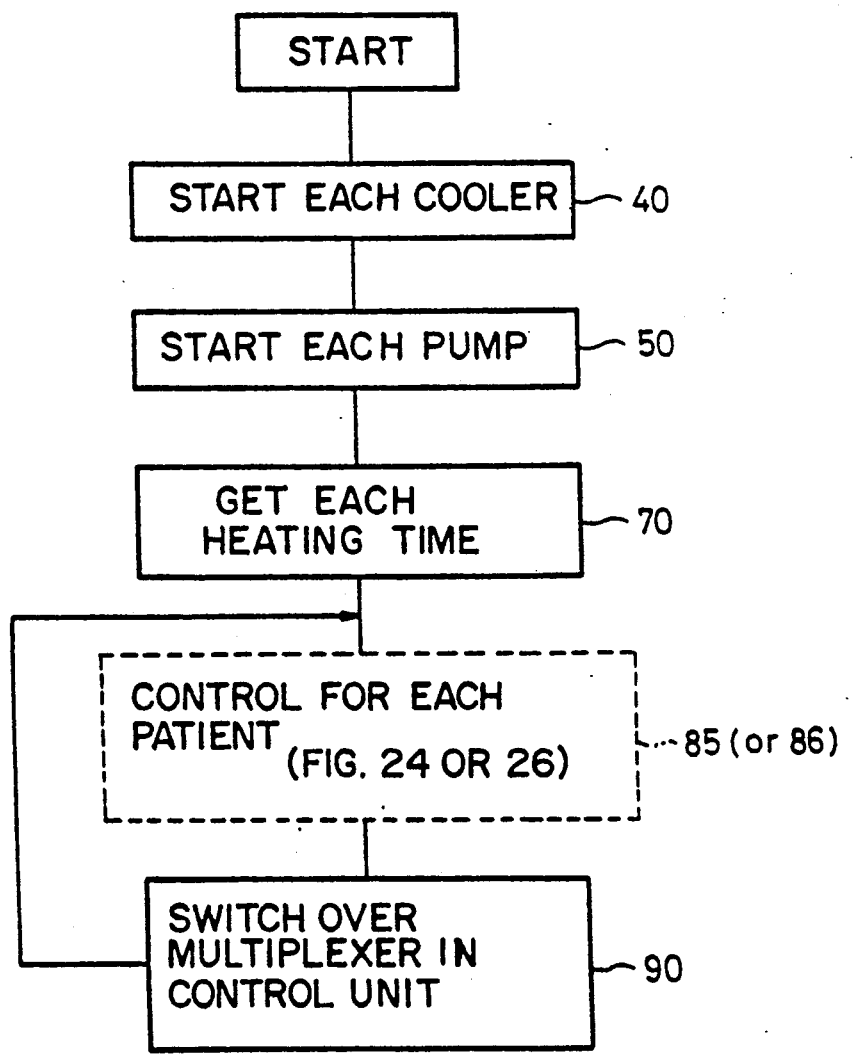
FIG. 23 is a flow chart which shows the operation of the embodiments respectively illustrated in FIGS. 22 and 25.

First, in manner similar to the above, each cooler 218 is started (Step 50 in FIG. 23). Then, the operator sets a heating time for each of the patients (Step 70 in FIG. 23). In the main control unit 16, control operations for individual patients are effected while being successively interchanged with each other by means of the multiplexer in synchronism with the clock pulses (see FIG. 5) (Steps 85 and 90 in FIG. 23).

Figure 24:
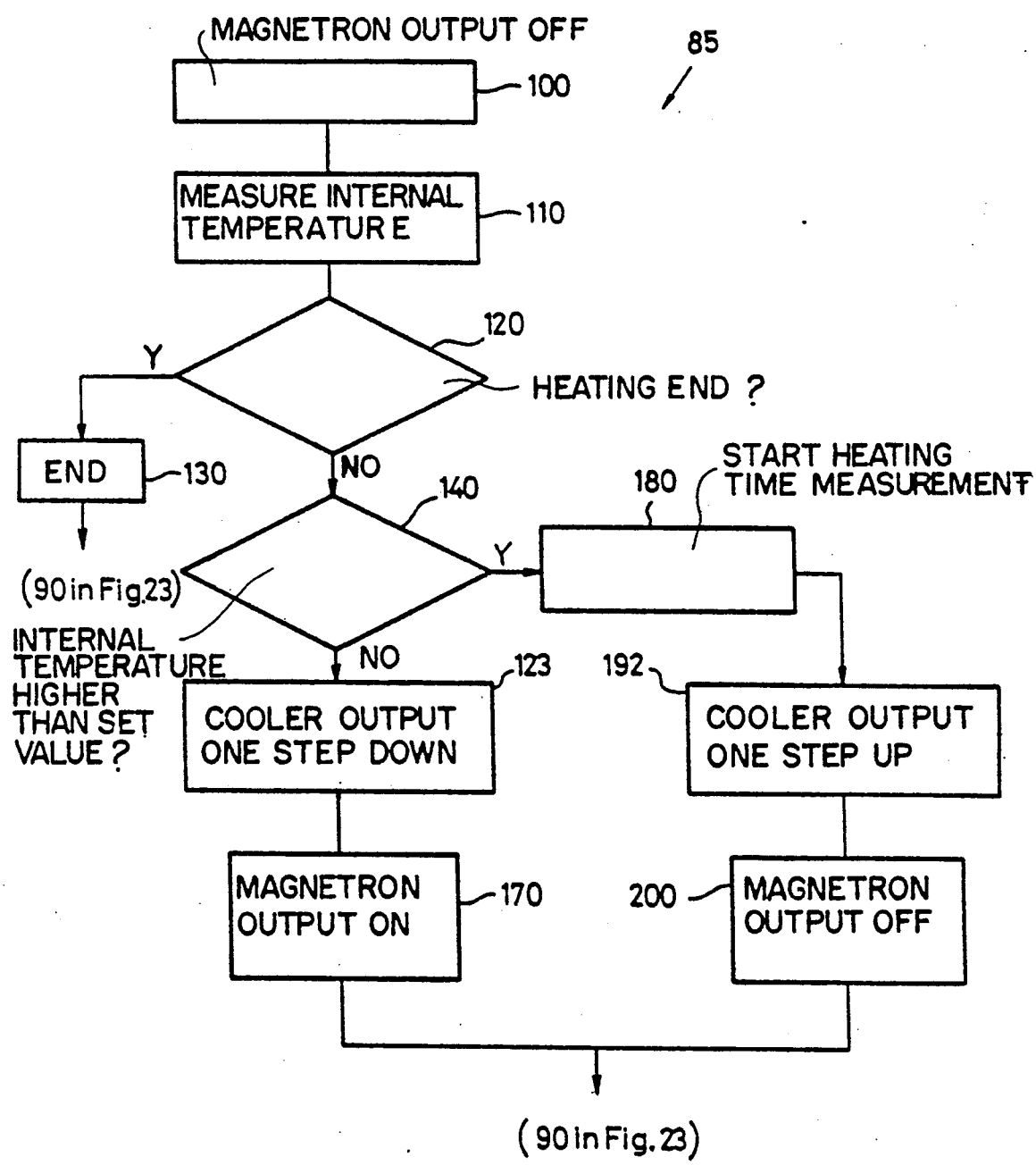
FIG. 24 is a flow chart which shows the operation of the embodiment illustrated in FIG. 22.

Among the above-described control operations, the control operation for each patient which is carried out in Step 85 is shown in the flow chart of FIG. 24. According to this flow chart, the output of each cooler 218 is individually stepped down (Step 123) or up (Step 192) by one degree in accordance with need, whereby the temperature of cooling water is controlled such that the surface temperature is maintained at the predetermined value (20° C). The other operations of this embodiment are the same as those of the fourth embodiment (see FIGS. 18 and 19).

Since this embodiment is arranged and operates as described above, it is possible to obtain advantageous effects which are substantially equivalent to those offered by the fourth embodiment. Since the coolers 218 are individually provided for the patients, there is no interference in terms of the temperature between the cooling water which is supplied to one patient and that which is supplied to another. Accordingly, designing of the system is facilitated, and it becomes possible to effect a precise control.

Seventh Embodiment

A seventh embodiment of the invention will be described hereinunder with reference to FIGS. 23, 25 and 26.

This invention aims at further accurately controlling the surface temperature of the body of each patient in addition to an object which is similar to that of the sixth embodiment.

Figure 25:
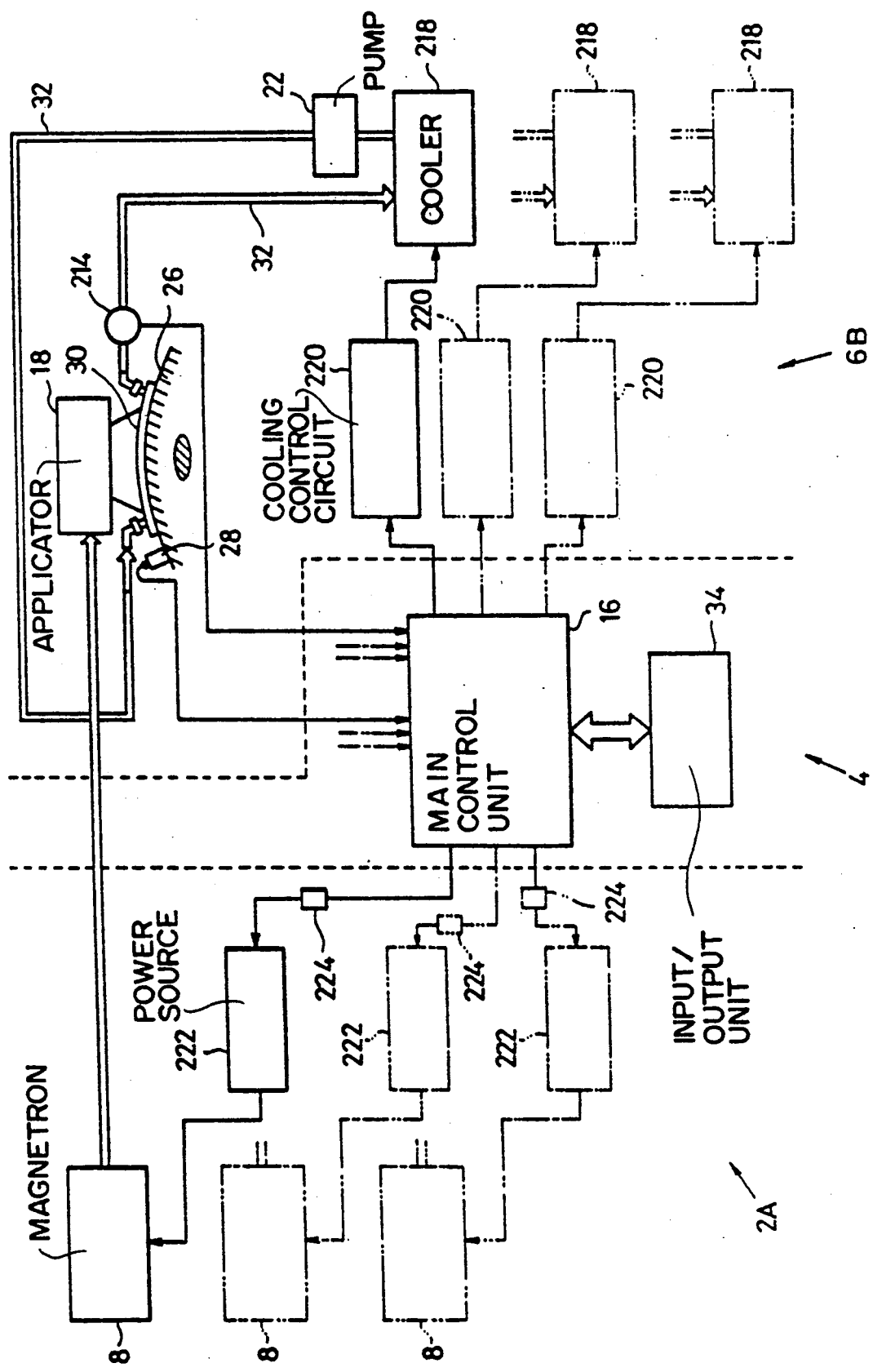
FIG. 25 is a general system diagram of a seventh embodiment of the invention.

To this end, as shown in FIG. 25, a coolant temperature sensor 214 (one which is the same as that employed in the second embodiment serving as a coolant temperature detecting means which detects the temperature of cooling water is additionally provided on the outlet side of the cooling member 30 of each applicator 18, and information detected by each coolant temperature sensor 214 is delivered to the main control unit 16. The arrangement of the other portion of this embodiment is the same as that of the sixth embodiment.

The following is a description of the general operation of this embodiment. It is to be noted that target values for the internal temperature and the surface temperature are respectively set at 43° C. and 20° C.

Figure 26:
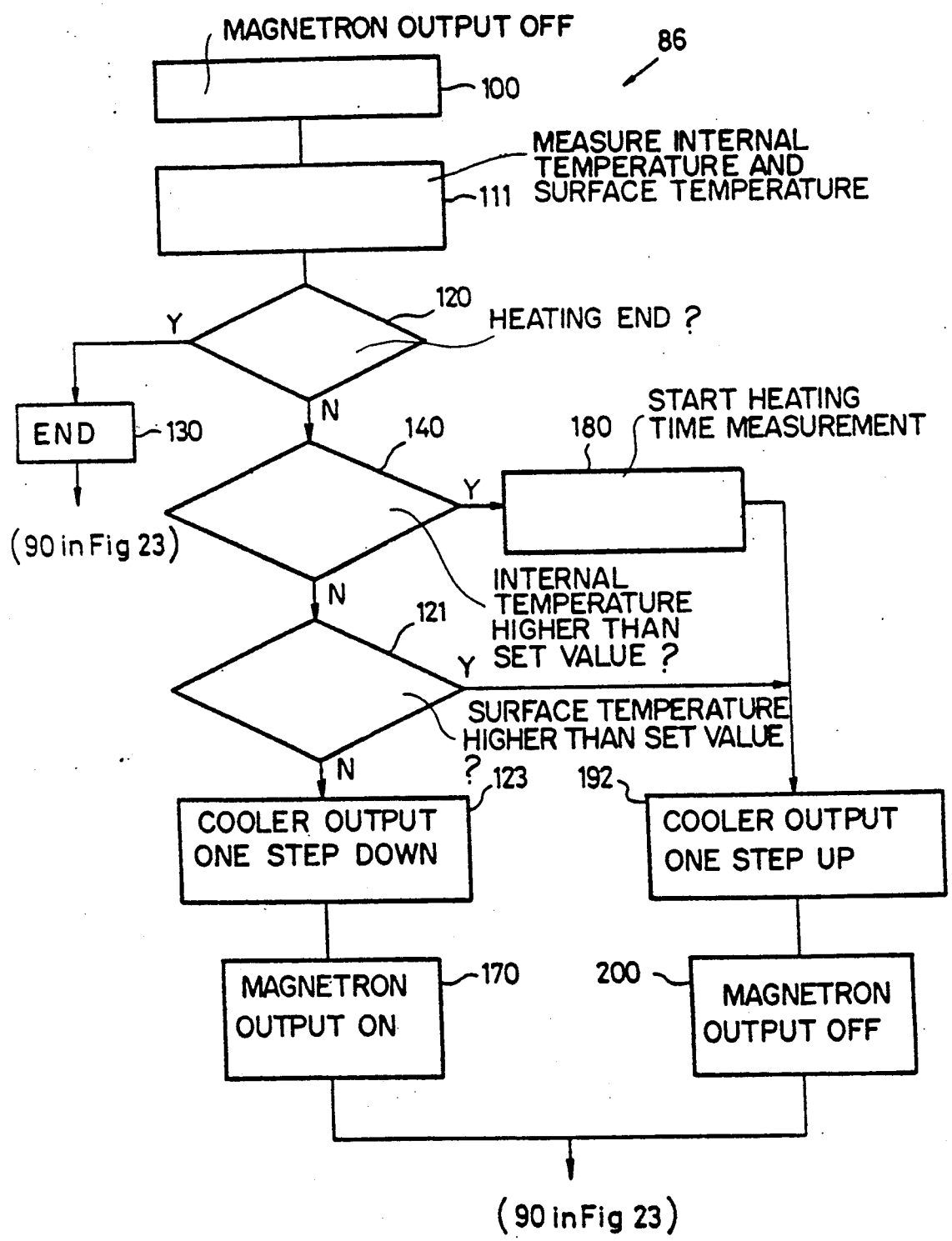
FIG. 26 is a flow chart which shows the operation of the embodiment illustrated in FIG. 25, in cooperation with the flow chart of FIG. 23.
Figure 27:
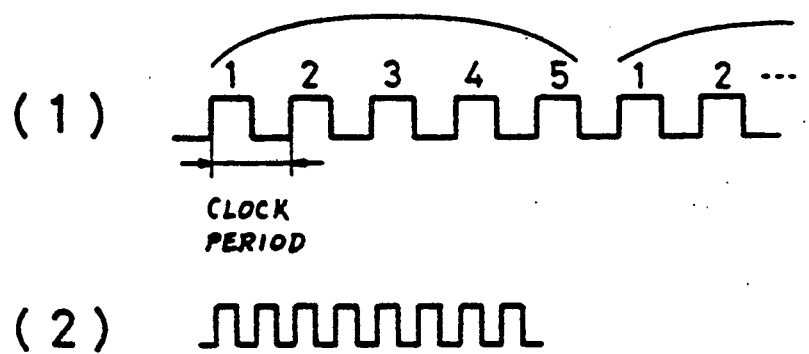
FIGS. 27(1) and 27(2) are timing charts which respectively show other examples of a clock pulse train.

The control process for this embodiment is shown in the flow chart of FIG. 23 which is described in relation to the sixth embodiment and in the flow chart of FIG. 26. According to these control flow charts, the following functions are added to those of the sixth embodiment.

(1) The main control unit 16 measures the surface temperature (Step 111 in FIG. 26).

(2) A judgement is made as to whether or not the surface temperature is higher than the set value (20° C.) (Step 121 in FIG. 26), and in accordance with the result of this judgement, the output of the cooler 218 concerned is stepped down (Step 123 in FIG. 26) or up (Step 192 in FIG. 26) by one degree through the corresponding cooling control circuit 220. The other operations of this embodiment are the same as those of the sixth embodiment.

As described above, it is also possible according to this embodiment to obtain advantageous effects which are equivalent to those offered by the sixth embodiment. Even when the surface temperature of the heated region undesirably fluctuates due to, for example, a change in the blood flow condition in the body of a patient, the surface temperature is controlled such as to immediately return to the set value. It is therefore advantageously possible to reliably prevent the occurrence of any thermal burn or the like and to alleviate pains which the patient may suffer. Since the coolant flow paths are separately and individually allotted to patients, there is no interference in terms of temperature between the cooling water supplied to one patient and that supplied to another. Accordingly, it is possible to effect a more stable control.

It is to be noted that, although the number of patients who are subjected to hyperthermia treatment is three in each of the above-described embodiments, the number of patients may be increased. In such a case (e.g., the number of patients is five), it is only necessary to change the clock pulse train shown in FIG. 5 into one such as that shown in FIG. 28(1). By controlling or varying the period of this clock pulse train, it is possible to determine a microwave irradiation period defined between two adjacent internal temperature measuring periods. Accordingly, if the period of the clock pulse train is reduced, the microwave irradiation interval is reduced correspondingly. It is therefore possible for an increased number of patients to be simultaneously subjected to hyperthermia treatment. Even in such a case, there is no hindrance to the treatment, since the internal temperature measuring period ($\Delta h$) is also set such as to be an extremely short period of time. Further, since the cost the magnetrons themselves is relatively low, it is possible to minimize the increase in the installation cost even if the number of patients in increased.

What is claimed is:

1. A heating apparatus for hyperthermia comprising:
   a plurality of electromagnetic wave generating means for generating electromagnetic waves, and respectively provided for a plurality of patients;
   a plurality of applicators respectively associated with the bodies of said patients;
   means for applying electromagnetic waves generated by said electromagnetic wave generating means to respective ones of said applicators for respectively irradiating the bodies of said patients with electromagnetic waves;
   a plurality of cooling members respectively associated with said applicators for cooling the bodies of patients with which the applicators are associated, each of said members having a coolant outlet side;
   coolant source means;
   means for supplying coolant from said source means to each of said cooling members;
   a plurality of coolant cooling means respectively provided for said cooling members, each coolant cooling means being adapted to cool down the coolant supplied to the corresponding one of said cooling members to a predetermined temperature;
   a plurality of internal temperature detecting means respectively associated with the bodies of said patients for detecting the temperature of a hyperthermia treatment region within a body irradiated with electromagnetic waves by the applicator associated with the body;
   a plurality of coolant temperature detecting means respectively associated with the cooling members, each of said coolant temperature detecting means being provided on the coolant outlet side of the cooling member for detecting the temperature of coolant flowing out therefrom; and
   main control unit means responsive to said internal temperature detecting means for independently controlling the operation of the respective electromagnetic wave generating means and the respective coolant cooling means.

2. A method for treating a region of a patient with microwaves in a treatment branch, said method comprising the steps of:
   a) generating microwaves;
   b) applying the generated microwaves to a treatment region of a patient;
   c) cooling the surface of said region using coolant that is cooled in a cooler whose cooling output is step-wise controllable;
   d) measuring the surface temperature of said region;
   e) reducing the output of the cooler by one step if the surface temperature is less than a preset value, or increasing the output of the cooler by one step if the surface temperature exceeds said preset value; and
   f) repeating steps c) through e).

3. A method according to claim 2 including the steps of:
   a) applying microwaves to said region at a power level that is step-wise controllable for a first predetermined period of time after which the power level is zero for a second predetermined period of time;
   b) measuring the internal temperature and surface temperature of said region while the power level is zero;
   c) increasing the power level by one step the next time microwaves are applied to said patient if the measured internal temperature is less than a preselected value if and only if the power level is less than a preselected value.

4. A method according to claim 3 including the step of beginning to time the heating of said region when the measured internal temperature exceeds said preselected value, and terminating the application of microwaves to said region after a preselected period of time.

5. A heating apparatus for hyperthermia comprising:
   a) a plurality of electromagnetic wave generation means for generating electromagnetic waves for treating a plurality of patients;
   b) a plurality of applicators, each of which is connected to a different electromagnetic wave generation means, wherein each applicator comprises means for irradiating different patients with sufficient electromagnetic waves to treat tumors of said patients;
   c) a plurality of cooling members, each of which is attached to one of said applicators, for cooling the bodies of said patients with coolant, said cooling members each having a coolant outlet and inlet, and wherein each cooling member comprises means for recirculating the coolant through said cooling members through their inlets and outlets;
   d) a plurality of coolers selectively operable for controlling the temperature of the recirculated coolant;
   e) a plurality of internal temperature detecting means, wherein each internal temperature detecting means comprises means for detecting the temperature of a hyperthermia treatment region within the body of a patient irradiated with electromagnetic waves by one of said applicator;
   f) a plurality of coolant temperature detecting means each provided on the coolant outlet of each of said coolant members for detecting the temperature of coolant flowing out therefrom; and
   g) a main control unit comprising means for: (1) receiving information from said internal temperature detecting means; (2) controlling the output of said electromagnetic wave generation means as a function of the temperature detected by the plurality of internal temperature detecting means; (3) receiving information from said coolant temperature detecting means; and (4) selectively operating said coolers as a function of the temperature of said coolant at the outlet side of said cooling members, wherein said main control unit, said plurality of cooling members, said plurality of coolers, and said plurality of generation means and applicators together comprise means for independently controlling the hyperthermia treatment of different patients.

6. Apparatus according to claim 5 wherein said control unit further comprises means for independently controlling the irradiation of each patient with electromagnetic waves by independently controlling the output of electromagnetic waves of each electromagnetic wave generation means.

7. Apparatus according to claim 6 wherein said control unit further comprises means for independently controlling the operation of each cooler.

8. Apparatus for treating a region of a patient using microwaves comprising:
   a) an applicator for irradiating a patient with microwaves;
   b) cooling means including a cooler for cooling coolant, a coolant loop for exchanging coolant between the applicator and the cooler, and a cooler control circuit for step-wise controlling the cooling output of said cooler;
   c) means for measuring the surface temperature of said region; and
   d) a control unit having means responsive to said surface temperature for reducing the output of the cooler by one step if the surface temperature is less than a preset value, or increasing the output of the cooler by one step if the surface temperature exceeds said preset value.

9. Apparatus according to claim 8 including:
   a) means for applying microwaves to said applicator at a power level that is step-wise controllable for a first predetermined period of time after which the power level is zero for a second predetermined period of time; and
   b) means for measuring the internal temperature of said region while the power level is zero;
   c) said control unit having means, responsive to measuring said internal temperature for increasing the power level by one step the next time microwaves are applied to said applicator if said internal temperature is less than a preselected value if and only if the power level is less than a preselected value.

10. An apparatus according to claim 9 including timer means responsive to the internal temperature for beginning to time the heating of said region when the measured internal temperature exceeds a preset value, and terminating the application of microwaves to said applicator after a preselected period of time.

* * * * *